United States Patent
Lehmann-Lintz et al.

(10) Patent No.: US 6,821,967 B2
(45) Date of Patent: Nov. 23, 2004

(54) SUBSTITUTED PIPERAZINE DERIVATIVES, THE PREPARATION THEREOF AND THEIR USE AS MEDICAMENTS

(75) Inventors: Thorsten Lehmann-Lintz, Ochsenhausen (DE); Armin Heckel, Biberach (DE); Leo Thomas, Biberach (DE); Michael Mark, Biberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/168,486

(22) PCT Filed: Dec. 16, 2000

(86) PCT No.: PCT/EP00/12843

§ 371 (c)(1),
(2), (4) Date: Oct. 9, 2002

(87) PCT Pub. No.: WO01/47898

PCT Pub. Date: Jul. 5, 2001

(65) Prior Publication Data

US 2003/0166637 A1 Sep. 4, 2003

(30) Foreign Application Priority Data

Dec. 27, 1999 (DE) .......................... 199 63 234

(51) Int. Cl.$^7$ .................. A61K 31/496; A61K 31/495; C07D 401/02; C07D 413/04; C07D 417/04
(52) U.S. Cl. .................. 514/218; 514/249; 514/252.17; 514/253.05; 514/253.06; 514/254.02; 514/254.06; 514/254.11; 514/255.03; 540/575; 544/292; 544/363; 544/356; 544/368; 544/370; 544/375; 544/380
(58) Field of Search .................. 544/380, 292, 544/363, 356, 368, 370, 375; 514/255.03, 218, 249, 252.17, 253.05, 253.06, 254.02, 254.06, 254.11; 540/575

(56) References Cited

U.S. PATENT DOCUMENTS

| 4,397,855 A | 8/1983 | Sircar |
| 5,712,279 A | 1/1998 | Biller et al. |

FOREIGN PATENT DOCUMENTS

| WO | WO 97 26240 | 7/1997 |
| WO | WO 00 61556 | 10/2000 |
| WO | WO 01 21604 A1 | 3/2001 |

*Primary Examiner*—Emily Bernhardt
(74) *Attorney, Agent, or Firm*—Robert P. Raymond; Michael Morris; David A. Dow

(57) ABSTRACT

The present invention relates to substituted piperazine derivatives of general formula

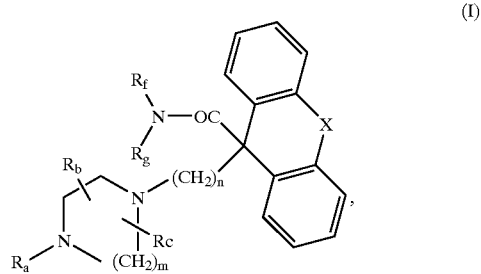

(I)

wherein $R_a$, $R_b$, $R_c$, $R_f$, $R_g$, X, m and n are defined as in claim 1, the isomers and salts thereof, particularly the physiologically acceptable salts thereof, which are valuable inhibitors of the microsomal triglyceride-transfer protein (MTP), medicaments containing these compounds and their use, as well as the preparation thereof.

7 Claims, No Drawings

SUBSTITUTED PIPERAZINE DERIVATIVES, THE PREPARATION THEREOF AND THEIR USE AS MEDICAMENTS

The present invention relates to substituted piperazine derivatives of general formula

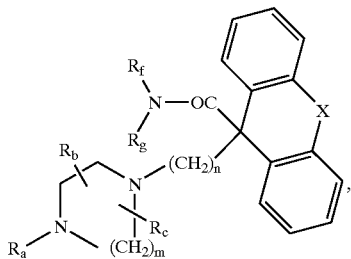

(I)

their isomers, their salts, particularly the physiologically acceptable salts thereof which have valuable pharmacological properties.

The compounds of the above general formula I are valuable inhibitors of the microsomal triglyceride-transfer protein (MTP) and are therefore suitable for lowering the plasma level of the atherogenic lipoproteins.

In the above general formula I m denotes the number 2 or 3, n denotes the number 1, 2, 3, 4 or 5, X denotes a carbon-carbon bond, an oxygen atom, a methylene, ethylene, imino or N—($C_{1-3}$-alkyl)-imino group, $R_a$ denotes a bi- or tri-nuclear aromatic hydrocarbon wherein an angular methyne group may be replaced by a nitrogen atom, a bi- or tri-nuclear heteroaromatic hydrocarbon linked to the piperazino group via a carbon atom, consisting of a 5-membered heteroaryl ring containing one or two nitrogen atoms and a cyclopentadienyl ring fused on via a vinylene group, wherein additionally a methyne group may be replaced by a nitrogen atom and/or an angular methyne group may be replaced by a nitrogen atom, a 5-membered heteroaryl ring which contains an imino group optionally substituted by a $C_{1-3}$-alkyl, phenyl-$C_{1-3}$-alkyl, phenyl, pyridinyl, pyridazinyl, pyrimidinyl or pyrazinyl group, or an oxygen or sulphur atom, and a phenyl or 6-membered heteroaryl ring fused on via one or two of the available vinylene groups, containing one, two or three nitrogen atoms, wherein the fused-on rings may be identical or different, or a naphthyl ring fused on via one of the two available vinylene groups, wherein additionally in a bicyclic or tricyclic group thus formed an angular carbon atom may be replaced by a nitrogen atom, or a 5-membered heteroaryl ring which contains an imino group optionally substituted by a $C_{1-3}$-alkyl, phenyl-$C_{1-3}$-alkyl, phenyl, pyridinyl, pyridazinyl, pyrimidinyl or pyrazinyl group, or an oxygen or sulphur atom, and one or two nitrogen atoms, and a phenyl, naphthyl, pyridine, pyridazine, pyrimidine or pyrazine ring fused on via the available vinylene group, wherein an angular carbon atom may be replaced by a nitrogen atom, a naphthyl or 6-membered heteroaryl ring containing one, two or three nitrogen atoms, and a pyridinyl, pyridazinyl, pyrimidinyl or pyrazinyl ring fused on via a vinylene group, wherein an angular carbon atom may be replaced by a nitrogen atom, or a phenyl ring and a 6-membered heteroaryl ring fused on via one or two of the available vinylene groups, containing one, two or three nitrogen atoms, wherein the fused-on rings may be identical or different and additionally in a bicyclic or tricyclic group thus formed an angular carbon atom may be replaced by a nitrogen atom, a pyridine, pyrazine or pyridazine ring and a phenyl or 6-membered heteroaryl ring fused on via the two available vinylene groups, containing one, two or three nitrogen atoms, wherein the fused-on rings may be identical or different and additionally in a tricyclic group thus formed an angular carbon atom may be replaced by a nitrogen atom, wherein the bi- and tricyclic groups mentioned above under $R_a$ may additionally be mono- or disubstituted in the carbon skeleton by a fluorine, chlorine, bromine or iodine atom, by a $C_{1-3}$-alkyl, hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, wherein the substituents may be identical or different and additionally the hydrogen atoms in the abovementioned alkyl and alkoxy moieties may be wholly or partly replaced by fluorine atoms, $R_b$ and $R_c$ independently of one another in each case denote a hydrogen atom or a $C_{1-3}$-alkyl group, $R_f$ and $R_g$, which may be identical or different, denote hydrogen atoms or $C_{1-6}$-alkyl groups wherein the hydrogen atoms may be wholly or partly replaced by fluorine atoms, $C_{3-7}$-cycloalkyl, phenyl, $C_{1-3}$-alkoxy-carbonyl-$C_{1-2}$-alkyl, carboxy-$C_{1-2}$-alkyl, methoxy-$C_{2-3}$-alkyl, heteroaryl, phenyl-$C_{1-3}$-alkyl or heteroaryl-$C_{1-3}$-alkyl groups, wherein the abovementioned phenyl and heteroaryl groups may be mono-, di- or tri-substituted in the carbon skeleton by fluorine, chlorine or bromine atoms, by $C_{1-3}$-alkyl or $C_{1-3}$-alkoxy groups wherein the hydrogen atoms may be wholly or partially replaced by fluorine atoms, by hydroxy, carboxy, $C_{1-3}$-alkoxycarbonyl, aminocarbonyl, $C_{1-3}$-alkyl-aminocarbonyl, N,N-di-($C_3$-alkyl)-aminocarbonyl, N,N-di-($C_{1-3}$-alkyl)-amino, nitro or amino groups, wherein the substituents may be identical or different, and/or a hydrogen atom bound to a nitrogen atom of the abovementioned heteroaryl groups may be replaced by a $C_{1-3}$-alkyl group wherein the hydrogen atoms may be wholly or partially replaced by fluorine atoms, by a $C_{1-3}$-alkyl-carbonyl or $C_{1-4}$-alkoxy-carbonyl group, or $R_f$ and $R_g$ together with the nitrogen atom between them denote a 3- to 7-membered cycloalkyleneimino group, wherein the methylene group in the 4 position in a 6- or 7-membered cycloalkyleneimino group may additionally be replaced by an oxygen or sulphur atom, by a sulphinyl, sulphonyl, imino or N-($C_{1-3}$-alkyl)-imino group, wherein the tricyclic group in the abovementioned general formula I may be mono- or disubstituted by fluorine or chlorine atoms, by methyl or methoxy groups and the substituents may be identical or different.

By the rings mentioned above in the definition of the group $R_a$ are meant the aromatic and heteroaromatic bi- and tricycles known from the literature, such as, for example, those described in "The Ring Index, Second Edition, A. M. Patterson, L. T. Capell, D. F. Walker, American Chemical Society 1960"; by a bi-nuclear ring, for example, is meant in particular the naphthyl, pyrrolo-pyrrole, benzofuran, pyrido-furan, pyridazino-furan, pyrimido-furan, pyrazino-furan, benzothiophene, pyrido-thiophene, pyridazino-thiophene, pyrimido-thiophene, pyrazino-thiophene, indole, pyrido-pyrrole, pyridazino-pyrrole, pyrimido-pyrrole, pyrazinopyrrole, benzo-pyrazole, pyrido-pyrazole, pyridazino-pyrazole, pyrimido-pyrazole, pyrazino-pyrazole, benzotriazole, pyrido-triazole, pyridazino-triazole, pyrimido-triazole, pyrazino-triazole, quinoline, isoquinoline, cinnoline, benzo-pyridazine, quinazoline, benzo-pyrimidine, quinoxaline, benzo-pyrazine, phthalazine, pyrido-pyridine, pyridazino-pyridine, pyrimido-pyridine, pyrazino-pyridine, benzoxazole, pyrido-oxazole, pyridazino-oxazole, pyrimidino-oxazole, pyrazino-oxazole, benzothiazole, pyrido-thiazole, pyridazino-thiazole, pyrimidino-thiazole, pyrazino-thiazole, benzimidazole, pyrido-imidazole, pyridazino-imidazole, pyrimidino-imidazole, pyrazino-imidazole, pteridine, triazolo-pyridine, triazolo-pyridazine, triazolo-pyrimidine, triazolo-pyrazine, pyridazino-pyrimidine, pyrimido-pyrimidine or pteridine ring and by a tri-nuclear ring is meant the phenanthene, anthracene, dibenzofuran, dibenzothiophene, acridine, phenanthridine, phenanthroline, phenanzine, naphtho-pyrrole, naphtho-pyrazole, naphtho-imidazole, naphtho-pyridine, naphtho-pyridazine, naphtho-pyrimidine or naphtho-pyrazine ring.

Moreover, the saturated alkyl and alkoxy moieties mentioned above in the definition which contain more than 2 carbon atoms also include the branched isomers thereof such as, for example, the isopropyl, tert.butyl, isobutyl group, etc.

Preferred compounds of the above general formula I are those wherein n denotes the number 3, 4 or 5 and m, X, $R_a$, $R_b$, $R_c$, $R_f$ and $R_g$ are as hereinbefore defined, the isomers and salts thereof.

Particularly preferred compounds of the above general formula I are those wherein m denotes the number 2 or 3, n denotes the number 3, 4 or 5, X denotes a carbon-carbon bond or an oxygen atom, $R_a$ denotes a bi- or tri-nuclear aromatic hydrocarbon wherein an angular methyne group may be replaced by a nitrogen atom, a bi- or tri-nuclear heteroaromatic hydrocarbon linked to the piperazino group via a carbon atom, consisting of a 5-membered heteroaryl ring which contains an imino group optionally substituted by a $C_{1-3}$-alkyl, phenyl-$C_{1-3}$-alkyl, phenyl, pyridinyl, pyridazinyl, pyrimidinyl or pyrazinyl group, or an oxygen or sulphur atom, and a phenyl or 6-membered heteroaryl ring fused on via one or two of the available vinylene groups, containing one, two or three nitrogen atoms, wherein the fused-on rings may be identical or different, or a naphthyl ring fused on via one of the two available vinylene groups, wherein additionally in a bicyclic or tricyclic group thus formed an angular carbon atom may be replaced by a nitrogen atom, or a 5-membered heteroaryl ring which contains an imino group optionally substituted by a $C_{1-3}$-alkyl, phenyl-$C_{1-3}$-alkyl, phenyl, pyridinyl, pyridazinyl, pyrimidinyl or pyrazinyl group, or an oxygen or sulphur atom, and one or two nitrogen atoms, and a phenyl, naphthyl, pyridine, pyridazine, pyrimidine or pyrazine ring fused on via the available vinylene group, wherein an angular carbon atom may be replaced by a nitrogen atom, a naphthyl or 6-membered heteroaryl ring containing one, two or three nitrogen atoms, and a pyridinyl, pyridazinyl, pyrimidinyl or pyrazinyl ring fused on via a vinylene group, wherein an angular carbon atom may be replaced by a nitrogen atom, or a phenyl ring and a 6-membered heteroaryl ring fused on via one or two of the available vinylene groups, containing one, two or three nitrogen atoms, wherein the fused-on rings may be identical or different and additionally in a bicyclic or tricyclic group thus formed an angular carbon atom may be replaced by a nitrogen atom, a pyridine, pyrazine or pyridazine ring and a phenyl or 6-membered heteroaryl ring fused on via the two available vinylene groups, containing one, two or three nitrogen atoms, wherein the fused-on rings may be identical or different and additionally in a tricyclic group thus formed an angular carbon atom may be replaced by a nitrogen atom, wherein the bi- and tricyclic groups mentioned above under $R_a$ may additionally be mono- or disubstituted in the carbon skeleton by a fluorine, chlorine, bromine or iodine atom, by a $C_{1-3}$-alkyl, hydroxy, $C_{1-3}$-alkoxy, carboxy, $C_{1-3}$-alkoxycarbonyl, aminocarbonyl, $C_{1-3}$-alkylaminocarbonyl or N,N-di-($C_{1-3}$-alkyl)-aminocarbonyl group, wherein the substituents may be identical or different and additionally the hydrogen atoms in the abovementioned alkyl and alkoxy moieties may be wholly or partly replaced by fluorine atoms, $R_b$ and $R_c$ independently of one another each denote a hydrogen atom or a methyl group, $R_f$ denotes a hydrogen atom, a $C_{1-6}$-alkyl group wherein the hydrogen atoms may be wholly or partly replaced by fluorine atoms, a $C_{3-7}$-cycloalkyl, $C_{1-3}$-alkoxy-carbonyl-$C_{1-2}$-alkyl, carboxy-$C_{1-2}$-alkyl, methoxy-$C_{2-3}$-alkyl, phenyl, heteroaryl, phenyl-$C_{1-3}$-alkyl or heteroaryl-$C_{1-3}$-alkyl group, wherein the abovementioned phenyl and heteroaryl groups may be mono-, di- or trisubstituted in the carbon skeleton by fluorine, chlorine or bromine atoms, by $C_{1-3}$-alkyl or $C_{1-3}$-alkoxy groups wherein the hydrogen atoms may be wholly or partially replaced by fluorine atoms, by hydroxy, nitro or amino groups, wherein the substituents may be identical or different, and/or a hydrogen atom bound to a nitrogen atom of the abovementioned heteroaryl groups may be replaced by a $C_{1-3}$-alkyl group wherein the hydrogen atoms may be wholly or partially replaced by fluorine atoms or by a $C_{1-3}$-alkyl-carbonyl or $C_{1-4}$-alkoxy-carbonyl group, and $R_g$ denotes a hydrogen atom, wherein the tricyclic group in the abovementioned general formula I may be mono- or disubstituted by fluorine or chlorine atoms or by methyl or methoxy groups and the substituents may be identical or different, in particular those compounds of general formula I wherein m denotes the number 2 or 3, n denotes the number 3, 4 or 5, X denotes a carbon-carbon bond or an oxygen atom, $R_a$ denotes a naphthyl, quinolinyl, quinazolinyl, quinoxalinyl, benzoxazolyl, benzothiazolyl, benzimidazolyl, pyrido-imidazolyl, pyrimido-imidazolyl, pyrido-pyridinyl or pyrimido-pyrimidinyl group, each of which is connected to the nitrogen atom of the adjacent piperazino group via a carbon atom contained in the bicyclic group, wherein the phenyl moiety of the abovementioned bicyclic groups may be monosubstituted by a trifluoromethyl or nitro group or mono- or disubstituted by fluorine, chlorine or bromine atoms or by methyl, methoxy or ethoxy groups, wherein the substituents may be identical or different, and any imino group present in the abovementioned bicyclic groups may additionally be substituted by a $C_{1-3}$-alkyl, phenyl-$C_{1-3}$-alkyl, phenyl or pyridyl group, $R_b$ and $R_c$ independently of one another each denote a hydrogen atom or a methyl group, $R_f$ denotes a hydrogen atom, a $C_{1-6}$-alkyl group wherein the hydrogen atoms may be wholly or partly replaced by fluorine atoms, a $C_{3-7}$-cycloalkyl, $C_{1-3}$-alkoxy-carbonyl-$C_{1-2}$-alkyl, carboxy-$C_{1-2}$-alkyl, methoxy-$C_{2-3}$-alkyl, phenyl, heteroaryl, phenyl-$C_{1-3}$-alkyl or heteroaryl-$C_{1-3}$-alkyl group, wherein the abovementioned phenyl and heteroaryl groups may each be mono- or disubstituted by fluorine, chlorine or bromine atoms, by $C_{1-3}$-alkyl or $C_{1-3}$-alkoxy groups wherein the hydrogen atoms may be wholly or partially replaced by fluorine atoms, by hydroxy, nitro or amino groups, wherein the substituents may be identical or different, and/or a hydrogen atom bound to a nitrogen atom of the abovementioned heteroaryl groups may be replaced by a $C_{1-3}$-alkyl group wherein the hydrogen atoms may be wholly or partially replaced by fluorine atoms, or by a $C_{1-3}$-alkyl-carbonyl group, and $R_g$ denotes a hydrogen atom, the isomers and salts thereof.

Most particularly preferred compounds of the above general formula I are those wherein m denotes the number 2, n denotes the number 4, X denotes a carbon-carbon bond or an oxygen atom, $R_a$ denotes a naphthyl, quinolinyl, quinazolinyl, benzoxazolyl, benzothiazolyl, benzimidazolyl or pyrido-imidazolyl group each of which is connected to the nitrogen atom of the adjacent piperazino group via a carbon atom contained in the bicyclic group, wherein any imino group present in the above-mentioned bicyclic groups may additionally be substituted by a $C_{1-3}$-alkyl, phenyl-$C_{1-3}$-alkyl, phenyl or pyridyl group, $R_b$ and $R_c$ independently of one another each denote a hydrogen atom or a methyl group, $R_f$ denotes a hydrogen atom, a $C_{1-6}$-alkyl group wherein the hydrogen atoms may be wholly or partly replaced by fluorine atoms, a $C_{3-7}$-cycloalkyl, $C_{1-3}$-alkoxy-carbonyl-$C_{1-2}$-alkyl, carboxy-$C_{1-3}$-alkyl, methoxy-$C_{2-3}$-alkyl, phenyl, heteroaryl, phenyl-$C_{1-3}$-alkyl or heteroaryl-$C_{1-3}$-alkyl group, wherein the abovementioned phenyl and heteroaryl groups may be substituted in each case by one or two fluorine, chlorine or bromine atoms or by one or two $C_{1-3}$-alkyl or $C_{1-3}$-alkoxy groups wherein the hydrogen atoms may be wholly or partially replaced by fluorine atoms, and $R_g$ denotes a hydrogen atom, the isomers and salts thereof.

According to the invention the new compounds are obtained by methods known from the literature, e.g. by the following methods:

a. Reacting a Compound of General Formula

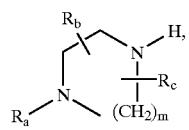

(II)

wherein m, $R_a$, $R_b$ and $R_c$ are as hereinbefore defined, with a compound of general formula

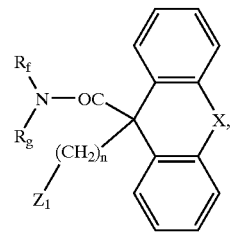

(III)

wherein n, $R_f$, $R_g$, X and the tricyclic ring are as hereinbefore defined and $Z_1$ denotes a nucleofugic leaving group such as a halogen atom, e.g. a chlorine, bromine or iodine atom.

The reaction is preferably carried out in a solvent such as methylene chloride, acetonitrile, tetrahydrofuran, toluene, acetone/water, dimethylformamide or dimethylsulphoxide, optionally in the presence of a base such as sodium hydride, potassium carbonate, potassium-tert.butoxide or N-ethyl-diisopropylamine at temperatures between 0 and 100° C., preferably at temperatures between 10 and 60° C.

b. Reacting a Compound of General Formula

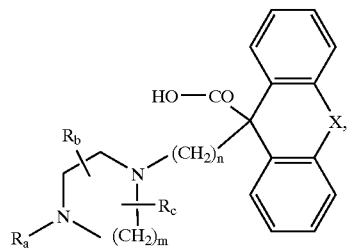

(IV)

wherein m, n, X, $R_a$, $R_b$, $R_c$ and the tricyclic ring are as hereinbefore defined, with an amine of general formula

(V)

wherein $R_f$ and $R_g$ are as hereinbefore defined, or with the reactive derivatives thereof.

The reaction is expediently carried out with a corresponding halide or anhydride of general formula IV in a solvent such as methylene chloride, chloroform, carbon tetrachloride, ether, tetrahydrofuran, dioxane, benzene, toluene, acetonitrile or sulpholane optionally in the presence of an inorganic or organic base at temperatures between −20 and 200° C., but preferably at temperatures between −10 and 160° C. It may, however, also be carried out with the free acid optionally in the presence of an acid-activating agent or a dehydrating agent, e.g. in the presence of isobutyl chloroformate, thionylchloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexyl-carbodiimide/N-hydroxysuccinimide or 1-hydroxy-benzotriazole, N,N'-carbonyldiimidazole or N,N'-thionyldiimidazole or tri-phenylphosphine/carbon tetrachloride, at temperatures between −20 and 200° C., but preferably at temperatures between −10 and 160° C.

If according to the invention a compound of general formula I is obtained which contains a nitro group, it may be converted by reduction into a corresponding amino compound, or if a compound of general formula I is obtained which contains an amino or imino group, it may be converted into a corresponding compound by alkylation.

The subsequent reduction of a nitro group is expediently carried out hydrogenolytically, e.g. with hydrogen in the presence of a catalyst such as platinum, palladium/charcoal or Raney nickel in a suitable solvent such as methanol, ethanol, ethyl acetate, tetrahydrofuran, dioxane, dimethylformamide or glacial acetic acid, optionally with the addition of an acid such as hydrochloric acid and at a hydrogen pressure of 1 to 7 bar, but preferably 1 to 5 bar, with metals such as iron, tin or zinc in the presence of an acid such as acetic acid or hydrochloric acid, with salts such as iron (II) sulphate, tin (II) chloride, sodium sulphide, sodium hydrogen sulphite or sodium dithionite, or with hydrazine in the presence of Raney nickel at temperatures between 0 and 100° C., but preferably at temperatures between 20 and 60° C.

The subsequent alkylation is optionally carried out in a solvent or mixture of solvents such as methylene chloride, dimethylformamide, benzene, toluene, chlorobenzene, tetrahydrofuran, benzene/tetrahydrofuran, dioxane, dimethylsulphoxide or sulpholane with an alkylating agent such as a corresponding halide or sulphonic acid ester, e.g. with methyl iodide, ethyl bromide, dimethylsulphate or benzyl chloride, optionally in the presence of a tertiary organic base or in the presence of an inorganic base, expediently at temperatures between 0 and 150° C., preferably at temperatures between 0 and 100° C.

In the reactions described hereinbefore, any reactive groups present such as hydroxy, carboxy, amino, alkylamino or imino groups may be protected during the reaction by conventional protecting groups which are cleaved again after the reaction.

For example, a protecting group for a hydroxy group may be a trimethylsilyl, tert.butyl-dimethylsilyl, acetyl, benzoyl, methyl, ethyl, tert.butyl, trityl, benzyl or tetrahydropyranyl group, a protecting group for a carboxyl group may be a trimethylsilyl, methyl, ethyl, tert.butyl, benzyl or tetrahydropyranyl group and protecting groups for an amino, alkylamino or imino group may be a formyl, acetyl, trifluoroacetyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C. However, a silyl group may also be cleaved using tetrabutylammonium fluoride as described hereinbefore.

However, a benzyl, methoxybenzyl or benzyloxycarbonyl group is cleaved for example hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution, optionally in the presence of a solvent such as tetrahydrofuran at temperatures between 0 and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents optically active acids in common use are e.g. the D- and L-forms of tartaric acid or dibenzoyltartaric acid, di-o-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid or maleic acid.

Moreover, if the new compounds of formula I thus obtained contain an acidic group such as a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to V used as starting materials are known from the literature in some cases or may be obtained by methods known from the literature or are described in the Examples.

A compound of general formula II is obtained for example by reacting a compound of general formula $R_a'$—Cl with a corresponding piperazine or homopiperazine wherein an imino group is substituted by the group $Z_2$ wherein $Z_2$ denotes a hydrogen atom or a protecting group for an amino group, for example the tert.butoxycarbonyl or benzyloxycarbonyl group, in a melt or in a solvent such as ethanol, dioxane or dimethylformamide in the presence of a base such as triethylamine and at temperatures between 0 and 130° C. The protecting group is cleaved by methods known from the literature and leads to a compound of general formula II.

A compound of general formula III is obtained for example by reacting a corresponding disubstituted carboxylic acid with a α,ω-dihaloalkane in the presence of a strong base such as lithium diisopropylamide, sodium amide or sodium hydride and subsequently reacting the carboxylic acid with a corresponding amine.

A compound of general formula IV is expediently obtained by reacting a correspondingly protected carboxylic acid derivative with a corresponding piperazine or homopiperazine.

As already mentioned hereinbefore, the compounds of general formula I and the physiologically acceptable salts thereof have valuable pharmacological properties. In particular, they are valuable inhibitors of the microsomal triglyceride-transfer protein (MTP) and are therefore suitable for lowering the plasma levels of the atherogenic lipoproteins.

For example, the compounds according to the invention were investigated for their biological effects as follows:

Inhibitors of MTP were identified by a cell-free MTP activity test. Solubilised liver microsomes from various species (e.g. rat, pig) can be used as the MTP source. To prepare the donor and acceptor vesicles, lipids dissolved in organic solvents were mixed in a suitable ratio and applied as a thin layer to the wall of glass container by blowing the solvent in a nitrogen current. The solution used to prepare donor vesicles contained 400 μM of phosphatidyl choline, 75 μM of cardiolipin and 10 μM of [$^{14}$C]-triolein (68.8 μCi/mg). To prepare the acceptor vesicles, a solution of 1.2 mM phosphatidyl choline, 5 μM triolein and 15 μM [$^3$H]-dipalmitoylphosphatidyl choline (108 mCi/mg) was used. Vesicles are produced by wetting the dried lipids with test buffer and subsequently ultrasonicating. Vesicle populations of uniform size were obtained by gel filtration of the ultrasonicated lipids. The MTP activity test contains donor vesicles, acceptor vesicles as well as the MTP source in test buffer. Substances were added from concentrated DMSO-containing stock solutions, the final concentration of DMSO in the test was 0.1%. The reaction was started by the addition of MTP. After a corresponding incubation time the transfer process was stopped by the addition of 500 μl of a SOURCE 30Q anion exchanger suspension (Pharmacia Biotech). The mixture was shaken for 5 minutes and the donor vesicles bound to the anion exchanger material were separated off by centrifuging. The radioactivity of [$^3$H] and [$^{14}$C] in the supernatant was determined by liquid scintillation measurement and from this the recovery of the acceptor vesicles and the triglyceride transfer speed was calculated.

In view of the abovementioned biological properties the compounds of general formula I and the physiologically acceptable salts thereof are particularly suitable for lowering the plasma concentration of atherogenic apolipoprotein B (apoB)-containing lipoproteins such as chylomicrons and/or very low density lipoproteins (VLDL) as well as the residues thereof such as low density lipoproteins (LDL) and/or lipoprotein(a) (Lp(a)), for treating hyperlipidaemias, for preventing and treating atherosclerosis and the clinical sequelae thereof, and for preventing and treating related disorders such as diabetes mellitus, adiposity and pancreatitis, oral administration being preferred.

The daily dose needed to achieve such an effect is between 0.5 and 500 mg, expediently between 1 and 350 mg, but preferably between 5 and 200 mg, in adults.

For this purpose, the compounds of formula I prepared according to the invention, optionally combined with other active substances such as other lipid-lowering agents, for example HMG-CoA-reductase-inhibitors, cholesterol biosynthesis inhibitors such as squalene synthase inhibitors and squalene cyclase inhibitors, bile acid-binding resins, fibrates, cholesterol resorption inhibitors, niacin, probucol, CETP inhibitors and ACAT inhibitors may be incorporated together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof in conventional galenic preparations such as plain or coated tablets, capsules, powders, suspensions or suppositories.

The Examples which follow are intended to illustrate the invention in more detail:

EXAMPLE 1

9-[4-(4-(benzothiazol-2-yl)-piperazin-1-yl)-butyl]-9H-fluorene-9-carboxylic acid-(2,2,2-trifluoro-ethyl)-amide a. 9-(4-bromo-butyl)-9H-fluorene-9-carboxylic acid 89 ml (0.11 mol) of a 1.6-Molar n-butyl-lithium solution in hexane are added dropwise to a solution of 21 g (0.1 mol) of 9-fluorenecarboxylic acid in 700 ml of tetrahydrofuran at 0° C. under nitrogen and stirred for one hour. Then, again at 0° C., 13.13 ml (0.11 mol) of dibromobutane are added and the solution is stirred for 30 hours at ambient temperature. After this time 50 ml of water are added and the mixture is stirred for 30 minutes. The solution is concentrated by evaporation, mixed with water and extracted with 250 ml of diethylether. The aqueous phase is acidified with 150 ml of 1N hydrochloric acid and extracted three times with 250 ml of dichloromethane. The combined organic phases are dried over sodium sulphate and the solvent is eliminated.

Yield: 18.5 g (53.6% of theory), Melting point: 123° C.

b. 9-(4-bromo-butyl)-9H-fluorene-9-carboxylic acid chloride 23 g (0.067 mol) of 9-(4-bromo-butyl)-9H-fluorene-9-carboxylic acid are dissolved in 40 ml of dichloromethane, and combined with three drops of dimethylformamide and 6.96 ml (0.081 mol) of oxalyl chloride, dissolved in 10 ml of dichloromethane, under nitrogen at 0° C. The mixture is stirred for 3 hours at ambient temperature. Then the solvent is eliminated and the crude product is reacted further without additional purification.

Yield: 24 g (99% of theory)

c. 9-(4-bromo-butyl)-9H-fluorene-9-carboxylic acid-(2,2,2-trifluoro-ethyl)-amide 23 g (0.063 mol) of 9-(4-bromo-butyl)-9H-fluorene-9-carboxylic acid chloride are added dropwise to a solution of 9.35 g (0.069 mol) of 2,2,2-trifluoroethylamine-hydrochloride and 26 ml (0.188 mol) of triethylamine in 550 ml of dichloromethane at 0° C. under nitrogen and stirred for 2 hours at ambient temperature. The reaction mixture is extracted twice each with water, 1N hydrochloric acid and sodium hydrogen carbonate solution. The organic phase is dried over sodium sulphate and the solvent is distilled off. The product is purified by column chromatography on silica gel (eluant: cyclohexane/ethyl acetate=8:1).

Yield: 15.8 g (58.6% of theory), Melting point: 172° C.

d. 2-(piperazin-1-yl)-benzothiazole

A solution of 1.7 g (0.01 mol) of 2-chlorobenzothiazole, 4.76 g (0.05 mol) of piperazine and 7 ml (0.05 mol) of triethylamine in 50 ml of ethanol is stirred for 48 hours at ambient temperature. The reaction mixture is concentrated by evaporation, mixed with water and extracted twice with dichloromethane. The combined organic phases are dried over sodium sulphate, the drying agent is filtered off and the filtrate is concentrated by evaporation. The residue is washed with diethylether.

Yield: 1.3 g (59.3% of theory), Melting point: decomposition from 279° C. $C_{11}H_{13}N_3S$ (M=219.31) Calc.: molecular peak $(M+H)^+$: 220. Found: molecular peak $(M+H)^+$: 220.

e. 9-[4-(4-(benzothiazol-2-yl)-piperazin-1-yl)-butyl]-9H-fluorene-9-carboxylic acid-(2,2,2-trifluoro-ethyl)-amide A suspension of 0.2 g (0.469 mmol) of 9-(4-bromo-butyl)-9H-fluorene-9-carboxylic acid-(2,2,2-trifluoro-ethyl)-amide, 0.17 g (0.775 mmol) of 2-(piperazin-1-yl)-benzothiazole, 0.1 g of potassium carbonate and 1 ml of water in 10 ml of acetonitrile is stirred for 10 hours at ambient temperature. The reaction mixture is then poured onto water, extracted with dichloromethane and the organic phase is dried over sodium sulphate. The product is purified by column chromatography on silica gel (eluant: dichloromethane/acetone =20:1, then dichloromethane/methanol=20:1).

Yield: 0.16 g (60.4% of theory), Melting point: 49–52° C. $C_{31}H_{31}F_3N_3OS$ (M=564.67) Calc.: molecular peak $(M+H)^+$: 565. Found: molecular peak $(M+H)^+$: 565.

The following compounds may be prepared analogously to Example 1:

(1) 9-{4-[4-(5-chloro-benzothiazol-2-yl)-piperazin-1-yl]-butyl}-9H-fluorene-9-carboxylic acid-(2,2,2-trifluoro-ethyl)-amide
(2) 9-{4-[4-(4-methoxy-benzothiazol-2-yl)-piperazin-1-yl]-butyl}-9H-fluorene-9-carboxylic acid-(2,2,2-trifluoro-ethyl)-amide
(3) 9-{4-[4-(6-fluoro-benzothiazol-2-yl)-piperazin-1-yl]-butyl}-9H-fluorene-9-carboxylic acid-(2,2,2-trifluoro-ethyl)-amide
(4) 9-{4-[4-(6-bromo-benzothiazol-2-yl)-piperazin-1-yl]-butyl}-9H-fluorene-9-carboxylic acid-(2,2,2-trifluoro-ethyl)-amide

EXAMPLE 2

9-[4-(4-(benzoxazol-2-yl)-piperazin-1-yl)-butyl]-9H-fluorene-9-carboxylic acid-(2,2,2-trifluoro-ethyl)-amide a. 2-(piperazin-1-yl)-benzoxazole A solution of 1.5 g (0.01 mol) of chlorobenzoxazole in 20 ml of dichloromethane is added dropwise at 0° C. to a solution of 1 g (0.012 mol) of piperazine and 7 ml (0.05 mol) of triethylamine in 10 ml of dichloromethane and the mixture is stirred for one hour at this temperature. Then it is extracted with water. The organic phase is dried over sodium sulphate, the drying agent is filtered off and the filtrate is concentrated by evaporation. The residue is washed with acetone.

Yield: 0.33 g (16.2% of theory), Melting point: >300° C. $C_{11}H_{13}N_3O$ (M=203.24) Calc.: molecular peak $(M+H)^+$: 204. Found: molecular peak $(M+H)^+$: 204.

b. 9-[4-(4-(benzoxazol-2-yl)-piperazin-1-yl)-butyl]-9H-fluorene-9-carboxylic acid-(2,2,2-trifluoro-ethyl)-amide A solution of 0.3 g (0.7 mmol) of 9-(4-bromo-butyl)-9H-fluorene-9-carboxylic acid-(2,2,2-trifluoro-ethyl)-amide, 0.2 g (0.98 mmol) of 2-(piperazin-1-yl)-benzoxazole and 1 ml of triethylamine in 10 ml of tetrahydrofuran is refluxed for 48 hours. The reaction mixture is then poured onto water, extracted twice with dichloromethane and the combined organic phases are dried over sodium sulphate. The product is purified by column chromatography on silica gel (eluant: cyclohexane/ethyl acetate=1:1).

Yield: 0.15 g (27.2% of theory), Melting point: 128° C. $C_{31}H_{31}F_3N_3O_2$ (M=548.61) Calc.: molecular peak $(M+H)^+$: 549. Found: molecular peak $(M+H)^+$: 549.

The following compounds may be prepared analogously to Example 2:

(1) 9-{4-[4-(5-methoxy-benzoxazol-2-yl)-piperazin-1-yl]-butyl}-9H-fluorene-9-carboxylic acid-(2,2,2-trifluoro-ethyl)-amide
(2) 9-{4-[4-(4-methyl-benzoxazol-2-yl)-.piperazin-1-yl]-butyl}-9H-fluorene-9-carboxylic acid-(2,2,2-trifluoro-ethyl)-amide

EXAMPLE 3

9-[4-(4-(quinolin-2-yl)-piperazin-1-yl)-butyl]-9H-fluorene-9-carboxylic acid-(2,2,2-trifluoro-ethyl)-amide a. 2-(piperazin-1-yl)-quinoline A suspension of 3.65 g (0.022 mol) of 2-chloroquinoline, 6.88 g (0.08 mol) of piperazine and 1.12 g (0.02 mol) of potassium carbonate in 150 ml of toluene is refluxed for five hours. After cooling it is extracted twice with water, the organic phase is dried over sodium sulphate and the solvent is concentrated by evaporation. The residue is combined with methanol. Then it is filtered and the filtrate is concentrated by evaporation.

b. 9-[4-(4-(quinolin-2-yl)-piperazin-1-yl)-butyl]-9H-fluorene-9-carboxylic acid-(2,2,2-trifluoro-ethyl)-amide Prepared analogously to Example 2b from 9-(4-bromo-butyl)-9H-fluorene-9-carboxylic acid-(2,2,2-trifluoro-ethyl)-amide and 2-(piperazin-1-yl-quinoline.

Yield: 0.14 g (35.6% of theory), Melting point: 56–57° C. $C_{33}H_{33}F_3N_4O$ (M=558.65) Calc.: molecular peak $(M+H)^+$: 559. Found: molecular peak $(M+H)^+$: 559.

The following compounds may be prepared analogously to Example 3:

(1) 9-{4-[4-(6-fluoro-quinolin-2-yl)-piperazin-1-yl]-butyl}-9H-fluorene-9-carboxylic acid-(2,2,2-trifluoro-ethyl)-amide (2) 9-{4-[4-(6-bromo-quinolin-2-yl)-piperazin-1-yl]-butyl}-9H-fluorene-9-carboxylic acid-(2,2,2-trifluoro-ethyl)-amide (3) 9-{4-[4-(6-trifluoromethyl-quinolin-2-yl)-piperazin-1-yl]-butyl}-9H-fluorene-9-carboxylic acid-(2,2,2-trifluoro-ethyl)-amide (4) 9-{4-[4-(6-methyl-quinolin-2-yl)-piperazin-1-yl]-butyl}-9H-fluorene-9-carboxylic acid-(2,2,2-trifluoro-ethyl)-amide (5) 9-{4-[4-(6-methoxy-quinolin-2-yl)-piperazin-1-yl]-butyl}-9H-fluorene-9-carboxylic acid-(2,2,2-trifluoro-ethyl)-amide (6) 9-{4-[4-(6-nitro-quinolin-2-yl)-piperazin-1-yl]-butyl}-9H-fluorene-9-carboxylic acid-(2,2,2-trifluoro-ethyl)-amide (7) 9-[4-(4-quinolin-2-yl-piperazin-1-yl)-pentyl]-9H-fluorene-9-carboxylic acid-(2,2,2-trifluoro-ethyl)-amide

EXAMPLE 4

9-[4-(4-quinolin-2-yl-piperazin-1-yl)-butyl]-9H-fluorene-9-carboxylic acid-(propyl)-amide a. 9-(4-bromo-butyl)-9H-fluorene-9-carboxylic acid-(propyl)-amide Prepared analogously to Example 1c from n-propylamine and 9-(4-bromo-butyl)-9H-fluorene-9-carboxylic acid chloride.

Yield: 1.4 g (52.7% of theory), Melting point: 46–48° C. $C_{21}H_{24}BrNO$ (M=386.33) Calc.: molecular peak $(M+H)^+$: 386/8. Found: molecular peak $(M+H)^+$: 386/8.

b. 9-[4-(4-quinolin-2-yl-piperazin-1-yl)-butyl]-9H-fluorene-9-carboxylic acid-(propyl)-amide Prepared analogously to Example 2b from 9-(4-bromo-butyl)-9H-fluorene-9-carboxylic acid-(propyl)-amide and 2-(piperazin-1-yl)-quinoline.

Yield: 0.14 g (34.7% of theory), $C_{34}H_{38}N_4O$ (M=518.70) Calc.: molecular peak $(M+H)^+$: 519. Found: molecular peak $(M+H)^+$: 519.

The following compound may be prepared analogously to Example 4:

(1) 9-{4-[4-(6-chloro-quinolin-2-yl)-piperazin-1-yl]-butyl}-9H-fluorene-9-carboxylic acid-(propyl)-amide

EXAMPLE 5

9-[4-(4-quinolin-2-yl-piperazin-1-yl)-butyl]-9H-fluorene-9-carboxylic acid-(benzyl)-amide a. 9-(4-bromo-butyl)-9H-fluorene-9-carboxylic acid-(benzyl)-amide Prepared analogously to Example 1c from benzylamine and 9-(4-bromo-butyl)-9H-fluorene-9-carboxylic acid chloride.

Yield: 2.1 g (71% of theory), $C_{25}H_{24}BrNO$ (M=434.38) Calc.: molecular peak $(M-H)^-$: 432/34. Found: molecular peak $(M-H)^-$: 432/34.

b. 9-[4-(4-quinolin-2-yl-piperazin-1-yl)-butyl]-9H-fluorene-9-carboxylic acid-(benzyl)-amide Prepared analogously to Example 2b from 9-(4-bromo-butyl)-9H-fluorene-9-carboxylic acid-(benzyl)-amide and 2-(piperazin-1-yl)-quinoline.

Yield: 0.12 g (30.6% of theory), $C_{38}H_{38}N_4O$ (M=566.75) Calc.: molecular peak $(M+H)^+$: 567. Found: molecular peak $(M+H)^+$: 567.

EXAMPLE 6

9-[4-(4-quinolin-2-yl-piperazin-1-yl)-butyl]-9H-fluorene-9-carboxylic acid-(ethyl)-amide a. 9-(4-bromo-butyl)-9H-fluorene-9-carboxylic acid-(ethyl)-amide Prepared analogously to Example 1c from ethylamine hydrochloride and 9-(4-bromo-butyl)-9H-fluorene-9-carboxylic acid chloride.

Yield: 2.25 g (87.9% of theory), $C_{20}H_{22}BrNO$ (M=372.30) Calc.: molecular peak $(M+H)^+$: 372/74. Found: molecular peak $(M+H)^+$: 372/74.

b. 9-[4-(4-quinolin-2-yl-piperazin-1-yl)-butyl]-9H-fluorene-9-carboxylic acid-(ethyl)-amide Prepared analogously to Example 2b from 9-(4-bromo-butyl)-9H-fluorene-9-carboxylic acid-(ethyl)-amide and 2-(piperazin-1-yl)-quinoline.

Yield: 0.09 g (22.1% of theory), $C_{33}H_{36}N_4O$ (M=504.68) Calc.: molecular peak $(M+H)^+$: 505. Found: molecular peak $(M+H)^+$: 505.

The following compound may be prepared analogously to Example 6:

(1) 9-{4-[4-(6-chloro-quinolin-2-yl)-piperazin-1-yl]-butyl}-9H-fluorene-9-carboxylic acid-(ethyl)-amide

EXAMPLE 7

9-[4-(4-quinolin-2-yl-piperazin-1-yl)-butyl]-9H-fluorene-9-carboxylic acid—(cyclopentyl)-amide a. 9-(4-bromo-butyl)-9H-fluorene-9-carboxylic acid-(cyclopentyl)-amide Prepared analogously to Example 1c from cyclopentylamine and 9-(4-bromo-butyl)-9H-fluorene-9-carboxylic acid chloride.

Yield: 2.05 g (72.3% of theory), $C_{23}H_{26}BrNO$ (M=412.37) Calc.: molecular peak $(M+H)^+$: 412/14. Found: molecular peak $(M+H)^+$: 412/14.

b. 9-[4-(4-quinolin-2-yl-piperazin-1-yl)-butyl]-9H-fluorene-9-carboxylic acid-(cyclopentyl)-amide Prepared analogously to Example 2b from 9-(4-bromo-butyl)-9H-fluorene-9-carboxylic acid-(cyclopentyl)-amide and 2-(piperazin-1-yl)-quinoline.

Yield: 0.18 g (45.5% of theory), $C_{36}H_{40}N_{40}$ (M=544.74) Calc.: molecular peak $M^+$: 544. Found: molecular peak $M^+$: 544.

EXAMPLE 8

9-[4-(4-quinolin-2-yl-piperazin-1-yl)-butyl]-9H-fluorene-9-carboxylic acid-(phenyl)-amide a. 9-(4-bromo-butyl)-9H-fluorene-9-carboxylic acid-(phenyl)-amide Prepared analogously to Example 1c from aniline and 9-(4-bromo-butyl)-9H-fluorene-9-carboxylic acid chloride.

Yield: 1.42 g (49.1% of theory), Melting point: 111–113° C. $C_{24}H_{22}BrNO$ (M=420.35) Calc.: molecular peak $(M-H)^-$: 418/20. Found: molecular peak $(M-H)^-$: 418/20.

b. 9-[4-(4-quinolin-2-yl-piperazin-1-yl)-butyl]-9H-fluorene-9-carboxylic acid-(phenyl)-amide Prepared analogously to Example 2b from 9-(4-bromo-butyl)-9H-fluorene-9-carboxylic acid-(phenyl)-amide and 2-(piperazin-1-yl)-quinoline.

Yield: 0.09 g (22.8% of theory), $C_{37}H_{36}N_4O$ (M=552.72) Calc.: molecular peak $M^+$: 552. Found: molecular peak $M^+$: 552.

The following compounds may be prepared analogously to Example 8:

(1) 9-[4-(4-quinolin-2-yl-piperazin-1-yl)-butyl]-9H-fluorene-9-carboxylic acid-(dimethylaminoethyl)-amide
(2) pyrrolidin-1-yl-{9-[4-(4-quinolin-2-yl-piperazin-1-yl)-butyl]-9H-fluoren-9-yl}-methanone
(3) morpholin-4-yl-{9-[4-(4-quinolin-2-yl-piperazin-1-yl)-butyl]-9H-fluoren-9-yl}-methanone
(4) 9-[4-(4-quinolin-2-yl-piperazin-1-yl)-butyl]-9H-fluorene-9-carboxylic acid-(ethyl-methyl)-amide

EXAMPLE 9

9-[4-(4-quinazolin-2-yl-piperazin-1-yl)-butyl]-9H-fluorene-9-carboxylic acid-(2,2,2-trifluoro-ethyl)-amide Prepared analogously to Example 2b from 9-(4-bromo-butyl)-9H-fluorene-9-carboxylic acid-(2,2,2-trifluoro-ethyl)-amide and 2-(piperazin-1-yl)-quinazoline.

Yield: 0.13 g (33% of theory), $C_{32}H_{32}F_3N_5O$ (M=559.64) Calc.: molecular peak $(M+H)^+$: 560. Found: molecular peak $(M+H)^+$: 560.

The following compounds may be prepared analogously to Example 9:

(1) 9-[4-(4-pyrido[2,3-d]pyrimidin-2-yl-piperazin-1-yl)-butyl]-9H-fluorene-9-carboxylic acid-(2,2,2-trifluoro-ethyl)-amide
(2) 9-[4-(4-pteridin-2-yl-piperazin-1-yl)-butyl]-9H-fluorene-9-carboxylic acid-(2,2,2-trifluoro-ethyl)-amide
(3) 9-[4-(4-pyrimido[4,5-d]pyrimidin-2-yl-piperazin-1-yl)-butyl-]-9H-fluorene-9-carboxylic acid-(2,2,2-trifluoro-ethyl)-amide
(4) 9-{4-[4-(9-methyl-9H-purin-2-yl)-piperazin-1-yl]-butyl}-9H-fluorene-9-carboxylic acid-(2,2,2-trifluoro-ethyl)-amide
(5) 9-[4-(4-[1.8]naphthyridin-2-yl-piperazin-1-yl)-butyl]-9H-fluorene-9-carboxylic acid-(2,2,2-trifluoro-ethyl)-amide

EXAMPLE 10

9-{4-[4-(1-methyl-benzimidazol-2-yl)-piperazin-1-yl]-butyl}-9H-fluorene-9-carboxylic acid-(2,2,2-trifluoro-ethyl)-amide a. 2-chloro-1-methyl-benzimidazole A solution of 5 g (0.032 mol) of 2-chlorobenzimidazole in 30 ml of dimethylformamide is combined at 0° C. with 1.4 g (0.033 mol) of sodium hydride (55%). After one hour 2.06 ml (0.033 mol) of methyl iodide are added dropwise and the mixture is stirred for one hour. Then the reaction mixture is mixed with water, the precipitate formed is filtered off and the product is recrystallised from petroleum ether.

Yield: 2.6 g (47.6% of theory)

b. 1-methyl-2-(piperazin-1-yl)-benzimidazole

A mixture of 1 g (6.02 mmol) of 2-chloro-1-methyl-benzimidazole and 2.58 g (30 mmol) of piperazine is heated to 150° C. without a solvent. The cooled melt is combined successively with water and dilute hydrochloric acid and extracted with dichloromethane. Then the aqueous phase is made alkaline with dilute sodium hydroxide solution and extracted with dichloromethane. The organic phase is dried over sodium sulphate and concentrated by evaporation. The product is purified by column chromatography on silica gel (eluant: dichloromethane/ethanol/ammonia=5:1:0.1).

Yield: 0.4 g (30.8% of theory), Melting point: 99° C. $C_{12}H_{16}N_4$ (M=216.28) Calc.: molecular peak $(M+H)^+$: 217. Found: molecular peak $(M+H)^+$: 217.

c. 9-{4-[4-(1-methyl-benzimidazol-2-yl)-piperazin-1-yl]-butyl}-9H-fluorene-9-carboxylic acid-(2,2,2-trifluoro-ethyl)-amide Prepared analogously to Example 1e from 9-(4-bromo-butyl)-9H-fluorene-9-carboxylic acid-(2,2,2-trifluoro-ethyl)-amide and 1-methyl-2-(piperazin-1-yl)-benzimidazole.

Yield: 0.24 g (46.2% of theory), Melting point: from 70° C. (foam) $C_{32}H_{34}F_3NO$ (M=561.65) Calc.: molecular peak $(M+H)^+$: 562. Found: molecular peak $(M+H)^+$: 562.

EXAMPLE 11

9-{4-[4-(1-ethyl-1H-benzimidazol-2-yl)-piperazin-1-yl]-butyl}-9H-fluorene-9-carboxylic acid-(2,2,2-trifluoro-ethyl)-amide Prepared analogously to Example 10 from 9-(4-bromo-butyl)-9H-fluorene-9-carboxylic acid-(2,2,2-trifluoro-ethyl)-amide and 1-ethyl-2-(piperazin-1-yl)-1H-benzimidazole.

Yield: 0.22 g (54.3% of theory), Melting point: 55° C. $C_{33}H_{36}F_3N_5O$ (M=575.68) Calc.: molecular peak $(M+H)^+$: 576. Found: molecular peak $(M+H)^+$: 576.

EXAMPLE 12

9-{4-[4-(1-Isopropyl-1H-benzimidazol-2-yl)-piperazin-1-yl]-butyl}-9H-fluorene-9-carboxylic acid-(2,2,2-trifluoro-ethyl)-amide Prepared analogously to Example 10 from 9-(4-bromo-butyl)-9H-fluorene-9-carboxylic acid-(2,2,2-trifluoro-ethyl)-amide and 1-isopropyl-2-(piperazin-1-yl)-1H-benzimidazole.

Yield: 0.27 g (55.9% of theory), $C_{34}H_{38}F_3N_5O$ (M=589.71) Calc.: molecular peak $(M+H)^+$: 590. Found: molecular peak $(M+H)^+$: 590.

EXAMPLE 13

9-{4-[4-(1-benzyl-1H-benzimidazol-2-yl)-piperazin-1-yl]-butyl}-9H-fluorene-9-carboxylic acid-(2,2,2-trifluoro-ethyl)-amide Prepared analogously to Example 10 from 9-(4-bromo-butyl)-9H-fluorene-9-carboxylic acid-(2,2,2-trifluoro-ethyl)-amide and 1-benzyl-2-(piperazin-1-yl)-1H-benzimidazole.

Yield: 0.3 g (95.4% of theory), Melting point: 60° C. $C_{38}H_{38}F_3N_5O$ (M=637.75) Calc.: molecular peak $(M+H)^+$: 638. Found: molecular peak $(M+H)^+$: 638.

EXAMPLE 14

9-{4-[4-(1-phenyl-1H-benzimidazol-2-yl)-piperazin-1-yl]-butyl}-9H-fluorene-9-carboxylic acid-(2,2,2-trifluoro-ethyl)-amide Prepared analogously to Example 10 from 9-(4-bromo-butyl)-9H-fluorene-9-carboxylic acid-(2,2,2-trifluoro-ethyl)-amide and 1-phenyl-2-(piperazin-1-yl)-1H-benzimidazole.

Yield: 0.38 g (86.5% of theory), Melting point: from 96° C. $C_{37}H_{36}F_3N_5O$ (M=623.72) Calc.: molecular peak $(M+H)^+$: 624. Found: molecular peak $(M+H)^+$: 624.

EXAMPLE 15

9-{4-[4-(3-methyl-3H-imidazo[4,5]pyridin-2-yl)-piperazin-1-yl]-butyl}-9H-fluorene-9-carboxylic acid-(2,2,2-trifluoro-ethyl)-amide a. tert.butyl 4-(3-methyl-3H-imidazo[4,5]pyridin-2-yl)-piperazin-1-carboxylate A solution of 3.83 g (0.011 mol)-2-chloro-3-methyl-3H-imidazo[4,5]pyridine, 2.2 g (0.012 mol) of 1-Boc-piperazine and 5 ml (0.029 mol) of ethyl-diisopropylamine in 15 ml of DMSO is stirred for 12 hours at 130° C. Water is added and the mixture is extracted with ethyl acetate. The combined organic phases are dried over sodium sulphate. The product is purified by column chromatography on silica gel (eluant: dichloromethane/acetone=20:1).

Yield: 2.74 g (78.5% of theory), $C_{16}H_{23}N_5O_2$ (M=317.39) Calc.: molecular peak $(M+H)^+$: 318. Found: molecular peak $(M+H)^+$: 318.

b. 3-methyl-2-piperazin-1-yl-3H-imidazo[4,5]pyridine

A solution of 2.74 g (8.63 mmol) of tert.butyl 4-(3-methyl-3H-imidazo[4,5]pyridin-2-yl)-piperazin-1-carboxylate and 3.5 ml of trifluoroacetic acid in 50 ml of dichloromethane is stirred for 14 hours while refluxing. Dilute sodium carbonate is added cautiously, the organic phase is separated off and the aqueous phase is extracted with dichloromethane. The combined organic phases are dried over sodium sulphate.

Yield: 1.3 g (69.3% of theory), $C_{11}H_{15}N_5$ (M=217.27) Calc.: molecular peak $(M+H)^+$: 218. Found: molecular peak $(M+H)^+$: 218.

c. 9-{4-[4-(3-methyl-3H-imidazo[4,5]pyridin-2-yl)-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 3-methyl-2-(piperazin-1-yl)-3H-imidazo[4,5]pyridine.

Yield: 0.28 g (70.7% of theory), Melting point: 60° C. $C_{31}H_{33}F_3N_6O$ (M=562.64) Calc.: molecular peak $(M+H)^+$: 563. Found: molecular peak $(M+H)^+$: 563.

EXAMPLE 16

9-{4-[4-(3-methyl-3H-imidazo[4,5]pyridin-5-yl)-piperazin-1-yl]-butyl}-9H-fluorene-9-carboxylic acid-(2,2,2-trifluoro-ethyl)-amide Prepared analogously to Example 15 from 5-chloro-3-methyl-3H-imidazo[4,5]pyridine and 9-(4-bromo-butyl)-9H-fluorene-9-carboxylic acid-(2,2,2-trifluoro-ethyl)-amide.

Yield: 0.02 g (5.8% of theory), $C_{31}H_{33}F_3N_6O$ (M=562.64) Calc.: molecular peak $(M)^+$: 562. Found: molecular peak $(M)^+$: 562.

EXAMPLE 17

9-{4-[4-(6-fluoro-1-methyl-1H-benzimidazol-2-yl)-piperazin-1-yl]-butyl}-9H-fluorene-9-carboxylic acid-(2,2,2-trifluoro-ethyl)-amide a. 6-fluoro-1-methyl-1,3-dihydro-benzimidazol-2-one A mixture of 6.9 g (32.38 mmol) of 4-fluoro-2-N-methylamino-aniline and 9.72 g (161.9 mmol) of urea is heated to 160° C. for one hour. After cooling, the residue is extracted with water and ethyl acetate. The organic phase is dried over sodium sulphate.

Yield: 4.1 g (76.2% of theory), b. 2-chloro-6-fluoro-1-methyl-1-benzimidazole

A suspension of 4.1 g (24.67 mmol) of 6-fluoro-1-methyl-1,3-dihydro-benzimidazol-2-one in 20 ml of phosphorus oxychloride is refluxed for two hours. After cooling, the solution is added dropwise to water, the precipitate formed is filtered off and washed with water. The mother liquor is extracted with dichloromethane. The organic phase is dried with sodium sulphate and the solvent is distilled off. The two products are combined.

Yield: 2 g (43.9% of theory), c. 6-fluoro-1-methyl-2-piperazin-1-yl-1H-benzimidazole Prepared analogously to Example 1 from 2-chloro-6-fluoro-1-methyl-1-benzimidazole and piperazine.

Yield: 1.57 g (61.9% of theory), $C_{12}H_{15}FN_4$ (M=234.27) Calc.: molecular peak $(M+H)^+$: 235.

Found: molecular peak $(M+H)^+$: 235.

d. 9-{4-[4-(6-fluoro-1-methyl-1H-benzimidazol-2-yl)-piperazin-1-yl]-butyl}-9H-fluorene-9-carboxylic acid-(2,2,2-trifluoro-ethyl)-amide Prepared analogously to Example 1e from 9-(4-bromo-butyl)-9H-fluorene-9-carboxylic acid-(2,2,2-trifluoro-ethyl)-amide and 6-fluoro-1-methyl-2-piperazin-1-yl-1H-benzimidazole Yield: 0.24 g (44.1% of theory), Melting point: 54° C. $C_{32}H_{33}F_4N_5O$ (M=579.64) Calc.: molecular peak $(M+H)^+$: 580. Found: molecular peak $(M+H)^+$: 580.

EXAMPLE 18

9-{4-[4-(5-fluoro-1-methyl-1H-benzimidazol-2-yl)-piperazin-1-yl]-butyl}-9H-fluorene-9-carboxylic acid-(2,2,2-trifluoro-ethyl)-amide Prepared analogously to Example 17 from 9-(4-bromo-butyl)-9H-fluorene-9-carboxylic acid-(2,2,2-trifluoro-ethyl)-amide and 5-fluoro-1-methyl-2-piperazin-1-yl-1H-benzimidazole Yield: 0.26 g (63.7% of theory), Melting point: 59° C. $C_{32}H_{33}F_4N_5O$ (M=579.64) Calc.: molecular peak $(M+H)^+$: 580. Found: molecular peak $(M+H)^+$: 580.

EXAMPLE 19

9-{4-[4-(5-chloro-1-methyl-1H-benzimidazol-2-yl)-piperazin-1-yl]-butyl}-9H-fluorene-9-carboxylic acid-(2,2,2-trifluoro-ethyl)-amide Prepared analogously to Example 18 from 9-(4-bromo-butyl)-9H-fluorene-9-carboxylic acid-(2,2,2-trifluoro-ethyl)-amide and 5-chloro-1-methyl-2-piperazin-1-yl-1H-benzimidazole Yield: 0.1 g (36.2% of theory), Melting point: 155° C. $C_{32}H_{33}ClF_3N_5O$ (M=596.10) Calc.: molecular peak $(M+H)^+$: 596/98. Found: molecular peak $(M+H)^+$: 596/98

EXAMPLE 20

9-{4-[4-(4-methoxy-1-methyl-1H-benzimidazol-2-yl)-piperazin-1-yl]-butyl}-9H-fluorene-9-carboxylic acid-(2,2,2-trifluoro-ethyl)-amide Prepared analogously to Example 2b from 9-(4-bromo-butyl)-9H-fluorene-9-carboxylic acid-(2,2,2-trifluoro-ethyl)-amide and 4-methoxy-1-methyl-2-piperazin-1-yl-1H-benzimidazole Yield: 0.14 g (33.6% of theory), Melting point: 146° C. $C_{33}H_{36}F_3N_5O_2$ (M=591.68) Calc.: molecular peak $(M-H)^-$: 590. Found: molecular peak $(M-H)^-$: 590.

EXAMPLE 21

9-{4-[4-(1H-benzimidazol-2-yl)-piperazin-1-yl]-butyl}-9H-fluorene-9-carboxylic acid-(2,2,2-trifluoro-ethyl)-amide a. tert.butyl 4-{4-[9-(2,2,2-trifluoro-ethylcarbamoyl)-9H-fluoren-9-yl]-butyl}-piperazine-1-carboxylate Prepared analogously to Example 2 from 9-(4-bromo-butyl)-9H-fluorene-9-carboxylic acid-(2,2,2-trifluoro-ethyl)-amide and Boc-piperazine.

Yield: 2.6 g (86.9% of theory), $C_{29}H_{36}F_3N_3O_3$ (M=531.62) Calc.: molecular peak (M+Na)$^+$: 554. Found: molecular peak (M+Na)$^+$: 554.

b. 9-(4-piperazin-1-yl-butyl)-9H-fluorene-9-carboxylic acid-(2,2,2-trifluoro-ethyl)-amide A solution of 2.3 g (4.32 mmol) of tert. butyl 4-{4-[9-(2,2,2-trifluoro-ethylcarbamoyl)-9H-fluoren-9-yl]-butyl}-piperazine-1-carboxylate and 6 ml of trifluoroacetic acid in 50 ml of dichloromethane is stirred for 14 hours at ambient temperature. Dilute sodium hydroxide solution is added cautiously, so that the solution has a pH of 9. The precipitate formed is filtered off, washed with water and dried.

Yield: 1.1 g (58.9% of theory)

c. 9-{4-[4-(1H-benzimidazol-2-yl)-piperazin-1-yl]-butyl}-9H-fluorene-9-carboxylic acid-(2,2,2-trifluoro-ethyl)-amide A mixture of 0.05 g (0.328 mmol) of 2-chloro-1H-benzimidazole and 0.21 g (0.487 mmol) of 9-(4-piperazin-1-yl-butyl)-9H-fluorene-9-carboxylic acid-(2,2,2-trifluoro-ethyl)-amide is heated to 150° C. for two hours. After cooling, the reaction mixture is dissolved in dichloromethane/ethanol. The product is purified by column chromatography on silica gel (eluant: dichloromethane/ethanol=20:1).

Yield: 0.05 g (18.7% of theory), Melting point: foam from 120° C. $C_{31}H_{32}F_3N_5O$ (M=547.62) Calc.: molecular peak (M+H)$^+$: 548. Found: molecular peak (M+H)$^+$: 548.

The following compounds may be prepared analogously to Examples 10–21:

(1) 9-{4-[4-(1-propyl-benzimidazol-2-yl)-piperazin-1-yl]-butyl}-9H-fluorene-9-carboxylic acid-(2,2,2-trifluoro-ethyl)-amide
(2) 9-{4-[4-(1-pyridin-2-yl-benzimidazol-2-yl)-piperazin-1-yl]-butyl}-9H-fluorene-9-carboxylic acid-2,2,2-trifluoro-ethyl)-amide
(3) 9-{4-[4-(1-methyl-benzimidazol-2-yl)-piperazin-1-yl]-butyl}-9H-fluorene-9-carboxylic acid-(ethyl)-amide
(4) 9-{4-[4-(1-methyl-benzimidazol-2-yl)-piperazin-1-yl]-butyl}-9H-fluorene-9-carboxylic acid-(benzyl)-amide
(5) 9-{4-[4-(6-chloro-1-methyl-benzimidazol-2-yl)-piperazin-1-yl]-butyl}-9H-fluorene-9-carboxylic acid-(2,2,2-trifluoro-ethyl)-amide
(6) 9-{4-[4-(5.6-dichloro-1-methyl-benzimidazol-2-yl)-piperazin-1-yl]-butyl}-9H-fluorene-9-carboxylic acid-(2,2,2-trifluoro-ethyl)-amide
(8) 9-{4-[4-(1-methyl-naphtho[2,3-d]imidazol-2-yl)-piperazin-1-yl]-butyl}-9H-fluorene-9-carboxylic acid-(2,2,2-trifluoro-ethyl)-amide
(7) 9-{4-[4-(1-methyl-benzimidazol-2-yl)-piperazin-1-yl]-propyl}-9H-fluorene-9-carboxylic acid-(2,2,2-trifluoro-ethyl)-amide
(8) 9-{4-[4-(1-methyl-benzimidazol-2-yl)-piperazin-1-yl]-pentyl}-9H-fluorene-9-carboxylic acid-(2,2,2-trifluoro-ethyl)-amide

EXAMPLE 22

9-[4-(4-quinoxalin-2-yl-piperazin-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-piperazin-1-yl-quinoxaline Yield: 0.24 g (60.9% of theory), Melting point: 142–145° C. $C_{32}H_{32}F_3N_5O$ (M=559.64) Calc.: molecular peak (M+H)$^+$: 560. Found: molecular peak (M+H)$^+$: 560.

EXAMPLE 23

9-{4-[4-(5-chloro-quinoxalin-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 5-chloro-2-piperazin-1-yl-quinoxaline Melting point: 74° C. $C_{32}H_{31}ClF_3N_5O$ (M=594.08) Calc.: molecular peak (M+H)$^+$: 594/596. Found: molecular peak (M+H)$^+$: 594/596.

EXAMPLE 24

9-{4-[4-(6-chloro-benzothiazol-2-yl)-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 6-chloro-2-piperazin-1-yl-benzothiazole.

Yield: 0.12 g (53.3% of theory), Melting point: 187° C. $C_{31}H_{30}ClF_3N_4OS$ (M=599.12) Calc.: molecular peak (M+H)$^+$: 599/601. Found: molecular peak (M+H)$^+$: 599/601.

EXAMPLE 25

9-{4-[4-(4-phenyl-quinolin-2-yl)-piperazin-1-yl]-butyl}-9H-fluorene-9-carboxylic acid-(2,2,2-trifluoro-ethyl)-amide Prepared analogously to Example 21 from 9-(4-piperazin-1-yl-butyl)-9H-fluorene-9-carboxylic acid-(2,2,2-trifluoro-ethyl)-amide and 2-chloro-4-phenyl-quinoline.

Yield: 0.06 g (22.7% of theory), Melting point: 105° C. $C_{39}H_{37}F_3N_5O$ (M=634.75) Calc.: molecular peak (M+H)$^+$: 635. Found: molecular peak (M+H)$^+$: 635.

EXAMPLE 26

9-{4-[4-(7-chloro-quinolin-2-yl)-piperazin-1-yl]-butyl}-9H-fluorene-9-carboxylic acid-(2,2,2-trifluoro-ethyl)-amide Prepared analogously to Example 21 from 9-(4-piperazin-1-yl-butyl)-9H-fluorene-9-carboxylic acid-(2,2,2-trifluoro-ethyl)-amide and 2,7-dichloro-quinoline.

Yield: 0.12 g (40% of theory), Melting point: 146–148° C. $C_{33}H_{32}ClF_3N_4O$ (M=593.09) Calc.: molecular peak (M+H)$^+$: 593/595. Found: molecular peak (M+H)$^+$: 593/595.

EXAMPLE 27

9-{4-[4-(5-chloro-quinolin-2-yl)-piperazin-1-yl]-butyl}-9H-fluorene-9-carboxylic acid-(2,2,2-trifluoro-ethyl)-amide Prepared analogously to Example 21 from 9-(4-piperazin-1-yl-butyl)-9H-fluorene-9-carboxylic acid-(2,2,2-trifluoro-ethyl)-amide and 2,5-dichloro-quinoline.

Yield: 0.025 g (10.4% of theory), Melting point: 142–143° C. $C_{33}H_{32}ClF_3N_4O$ (M=593.09) Calc.: molecular peak (M+H)$^+$: 593/595. Found: molecular peak (M+H)$^+$: 593/595.

EXAMPLE 28

9-{4-[4-(6-chloro-quinolin-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 6-chloro-2-piperazin-1-yl-quinoline.

Yield: 0.06 g (14.4% of theory), Melting point: 151° C. $C_{33}H_{32}ClF_3N_4O$ (M=593.09) Calc.: molecular peak (M+H)$^+$: 593/595. Found: molecular peak (M+H)$^+$: 593/595.

EXAMPLE 29

9-{4-[4-(8-chloro-quinolin-2-yl)-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 8-chloro-2-piperazin-1-yl-quinoline.

Yield: 0.16 g (38.3% of theory), Melting point: 121° C. $C_{33}H_{32}ClF_3N_4O$ (M=593.09) Calc.: molecular peak (M+H)$^+$: 593/595. Found: molecular peak (M+H)$^+$: 593/595.

EXAMPLE 30

9-{4-[4-(8-methoxy-quinolin-2-yl)-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 8-methoxy-2-piperazin-1-yl-quinoline.

Yield: 0.31 g (37.4% of theory), Melting point: 74° C. $C_{34}H_3F_3N_4O_2$ (M=588.67) Calc.: molecular peak (M–H)$^-$: 587. Found: molecular peak (M–H)$^-$: 587.

EXAMPLE 31

9-{4-[4-(8-hydroxy-quinolin-2-yl)-piperazin-1-yl]-butyl}-9H-fluorene-9-carboxylic acid-(2,2,2-trifluoro-ethyl)-amide A solution of 0.2 g (0.34 mmol) of 9-{4-[4-(8-methoxy-quinolin-2-yl)-piperazin-1-yl]-butyl}-9H-fluorene-9-carboxylic acid-(2,2,2-trifluoro-ethyl)-amide and 0.16 ml (1.7 mmol) of boron tribromide in 20 ml of dichloromethane is stirred for 48 hours at ambient temperature. The reaction solution is extracted with water and dichloromethane, dried over sodium sulphate and the solvent is distilled off. The product is purified by column chromatography on silica gel (eluant: ethyl acetate/methanol=50:1).

Yield: 0.03 g (15.4% of theory), Melting point: 159° C. $C_{33}H_{33}F_3N_4O_2$ (M=574.65) Calc.: molecular peak (M+H)$^+$: 575. Found: molecular peak (M+H)$^+$: 575.

EXAMPLE 32

9-{4-[4-(8-bromo-quinolin-2-yl)-piperazin-1-yl]-butyl}-9H-fluorene-9-carboxylic acid-(2,2,2-trifluoro-ethyl)-amide a. N-(2-bromo-phenyl)-3-ethoxy-acrylamide 10 g (74.31 mmol) of 3-ethoxy-acryloyl-chloride are added dropwise at 0° C. to a solution of 11.6 g (67.43 mmol) of 2-bromo-aniline in 60 ml of pyridine and stirred for one hour at this temperature. The mixture is allowed to come up to ambient temperature and stirred for two hours. Then the reaction mixture is extracted with water and ethyl acetate. The organic phase is extracted with water and 1 N hydrochloric acid, combined with activated charcoal and dried over sodium sulphate. The solvent is distilled off and the residue is recrystallised from isopropanol/water 2:1.

Yield: 6.5 g (35.7% of theory), Melting point: 98° C.

b. 8-bromo-1H-quinoline-2-one 6 g (22.21 mmol) of N-(2-bromo-phenyl)-3-ethoxy-acrylamide are added batchwise to 30 ml of concentrated sulphuric acid (exothermic) and stirred for one hour. The reaction mixture is poured onto ice water and the precipitate formed is filtered off. The product is purified by column chromatography on silica gel (eluant: dichloromethane/ethyl acetate=3:1).

Yield: 2.95 g (59.3% of theory), Melting point: 186° C. $C_9H_6BrNO$ (M=224.05) Calc.: molecular peak (M)$^+$: 222/224. Found: molecular peak (M)$^+$: 222/224.

c. 8-bromo-2-chloro-quinoline

A suspension of 2.8 g (12.49 mmol) of 8-bromo-1H-quinoline-2-one in 20 ml of phosphorus oxychloride is refluxed for 90 minutes and the reaction mixture is cooled and then added dropwise to 200 ml of water. The aqueous solution is made basic with concentrated ammonia solution, the precipitate formed is filtered off and washed with water.

Yield: 2.8 g (92.4% of theory), Melting point: 115° C. $C_9H_6BrClN$ (M=242.50) Calc.: molecular peak (M)$^+$: 241/243/245. Found: molecular peak (M)$^+$: 241/243/245.

d. 8-bromo-2-piperazin-1-yl-quinoline

Prepared analogously to Example 3 from 8-bromo-2-chloro-quinoline and piperazine.

Yield: 1.5 g (83% of theory), $C_{13}H_{14}BrN_3$ (M=292.81) Calc.: molecular peak (M+H)$^+$: 292/294. Found: molecular peak (M+H)$^+$: 292/294.

e. 9-{4-[4-(8-bromo-quinolin-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 8-bromo-2-piperazin-1-yl-quinoline.

Yield: 0.44 g (42% of theory), Melting point: 66° C. $C_{33}H_{32}BrF_3N_4O$ (M=637.54) Calc.: molecular peak (M+H)$^+$: 637/639. Found: molecular peak (M+H)$^+$: 637/639.

EXAMPLE 33

9-{4-[4-(8-phenyl-quinolin-2-yl)-piperazin-1-yl]-butyl}-9H-fluorene-9-carboxylic acid-(2,2,2-trifluoro-ethyl)-amide A reaction mixture of 0.2 g (0.314 mmol) of 9-{4-[4-(8-bromo-quinolin-2-yl)-piperazin-1-yl]-butyl}-9H-fluorene-9-carboxylic acid-(2,2,2-trifluoro-ethyl)-amide, 0.033 g (0.267 mmol) of phenylboric acid, 0.018 g (0.016 mmol) of tetrakis triphenyl palladium and 0.2 ml of a 2 M sodium carbonate solution in 3 ml of toluene is refluxed for 20 hours under nitrogen. The solvent is distilled off. The residue is purified by column chromatography on silica gel (eluant: cyclohexane/ethyl acetate=3:2).

Yield: 0.06 g (30% of theory), $C_{39}H_{37}F_3N_4O$ (M=634.75) Calc.: molecular peak (M+H)$^+$: 635. Found: molecular peak (M+H)$^+$: 635.

EXAMPLE 34

9-{4-[4-(4-methyl-quinolin-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 4-methyl-2-piperazin-1-yl-quinoline.

Yield: 0.23 g (42.8% of theory), $C_{34}H_{35}F_3N_4O$ (M=572.67) Calc.: molecular peak (M+H)$^+$: 573. Found: molecular peak (M+H)$^+$: 573.

EXAMPLE 35

9-{4-[4-(3-methyl-quinolin-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 3-methyl-2-piperazin-1-yl-quinoline.

Yield: 0.09 g (22.3% of theory), $C_{34}H_35F_3N_4O$ (M=572.67) Calc.: molecular peak (M+H)$^+$: 573. Found: molecular peak (M+H)$^+$: 573.

EXAMPLE 36

9-{4-[4-(8-methoxy-quinolin-2-yl)-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 1-methoxy-3-piperazin-1-yl-isoquinoline.

Yield: 0.08 g (16.5% of theory), Melting point: 67° C. $C_{34}H_{35}F_3N_4O_2$ (M=588.67) Calc.: molecular peak (M+H)$^+$: 589. Found: molecular peak (M+H)$^+$: 589.

EXAMPLE 37

9-{4-[4-(8-ethoxy-naphthalen-2-yl)-piperazin-1-yl]-butyl}-9H-fluorene-9-carboxylic acid-(2,2,2-trifluoro-ethyl)-amide a. 7-(4-benzyl-piperazin-1-yl)-naphthalen-1-ol A suspension of 25 g (0.156 mol) of naphthalene-1,7-diol, 35 ml (0.202 mol) of 1-benzyl-piperazine and 60 g (0.316 mol) of sodium disulphite in 250 ml of water is refluxed for four days under nitrogen. After cooling, the precipitate is filtered off, washed with water and dried in a drying cupboard.

Yield: 37.18 g (74.8% of theory), $C_{21}H_{22}N_2O$ (M=318.42) Calc.: molecular peak (M+H)$^+$: 319. Found: molecular peak (M+H)$^+$: 319.

b. 1-benzyl-4-(8-ethoxy-naphthalen-2-yl)-piperazine

A suspension of 37 g (0.116 mol) of 7-(4-benzyl-piperazin-1-yl)-naphthalen-1-ol and 15 g (0.134 mol) of potassium tert.butoxide in 150 ml of dimethylformamide is stirred for 30 minutes at ambient temperature and then slowly combined with 11 ml (0.135 mol) of ethyl iodide. It is then stirred for 14 hours at ambient temperature. Then the reaction mixture is concentrated by evaporation and the residue is extracted with dichloromethane and water. It is filtered through aluminium oxide, dried over sodium sulphate and the solvent is distilled off. The residue is recrystallised from isopropanol.

Yield: 34 g (84.5% of theory), Melting point: 60–62° C. $C_{23}H_{26}N_2O$ (M=346.47) Calc.: molecular peak (M+H)$^+$: 347. Found: molecular peak (M+H)$^+$: 347.

c. 1-(8-ethoxy-naphthalen-2-yl)-piperazine

A solution of 24.9 g (0.072 mol) of 1-benzyl-4-(8-ethoxy-naphthalen-2-yl)-piperazine in 360 ml of ethanol is combined with 5 g of palladium on charcoal (10%) and stirred at a hydrogen pressure of 5 bar at ambient temperature. The catalyst is separated off, the filtrate is concentrated by evaporation and the residue is washed with diethylether.

Yield: 15.5 g (84% of theory), Melting point: 158–161° C. $C_{16}H_{20}N_2O$ (M=256.35) Calc.: molecular peak (M+H)$^+$: 257. Found: molecular peak (M+H)$^+$: 257.

d. 9-{4-[4-(8-ethoxy-naphthalen-2-yl)-piperazin-1-yl]-butyl}-9H-fluorene-9-carboxylic acid-(2,2,2-trifluoro-ethyl)-amide A suspension of 0.5 g (1.17 mmol) of 9-(4-bromo-butyl)-9H-fluorene-9-carboxylic acid-(2,2,2-trifluoro-ethyl)-amide, 0.3 g (1.17 mmol) of 1-(8-ethoxy-naphthalen-2-yl)-piperazine and 1 g (7 mmol) of potassium carbonate in 50 ml of dimethylformamide is stirred for 14 hours at 90° C. The reaction mixture is poured onto water and the precipitate is filtered off. The product is purified by column chromatography on silica gel (eluant: cyclohexane/ethyl acetate=3:2).

Yield: 0.18 g (29.9% of theory), $C_{36}H_{38}F_3N_3O_2$ (M=601.71) Calc.: molecular peak M$^+$: 601. Found: molecular peak M$^+$: 601.

EXAMPLE 38

9-{4-[(S)-2-methyl-4-quinolin-2-yl-piperazin-1-yl]-butyl}-9H-fluorene-9-carboxylic acid-(2,2,2-trifluoro-ethyl)-amide a. 2-[(S)-3-methyl-piperazin-1-yl]-quinoline A solution of 1.554 g (9.5 mmol) of 2-chloroquinoline and 1 g (9.984 mmol) of (S)-2-methylpiperazine in 10 ml of n-butanol is stirred for three hours at 130° C. Then the solvent is distilled off. The residue is purified by column chromatography on silica gel (eluant: dichloromethane/ethanol/ammonia=20:1:0.1).

Yield: 1.3 g (60.2% of theory), $C_{14}H_{17}N_3$ (M=227.312) Calc.: molecular peak (M+H)$^+$: 228. Found: molecular peak (M+H)$^+$: 228.

b. 9-{4-[(S)-2-methyl-4-quinolin-2-yl-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-[(S)-3-methyl-piperazin-1-yl]-quinoline Yield: 0.4 g (56.6% of theory), Melting point: 102° C. $C_{34}H_{35}F_3N_4O$ (M=572.67) Calc.: molecular peak (M+H)$^+$: 573. Found: molecular peak (M+H)$^+$: 573.

EXAMPLE 39

9-{4-[(R)-2-methyl-4-quinolin-2-yl-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-[(R)-3-methyl-piperazin-1-yl]-quinoline Yield: 0.25 g (35.4% of theory), Melting point: 102° C. $C_{34}H_{35}F_3N_4O$ (M=572.67) Calc.: molecular peak (M+H)$^+$: 573. Found: molecular peak (M+H)$^+$: 573.

EXAMPLE 40 a. Tert.butyl 3-methyl-4-quinolin-2-yl-piperazine-1-carboxylate

A reaction mixture of 1 g (4.99 mmol) of tert.butyl 3-methyl-piperazine-1-carboxylate, 0.588 g (3.6 mmol) of 2-chloroquinoline and 0.498 g (3.6 mmol) of potassium carbonate is heated to 130° C. for three hours. Then the solvent is distilled off. The residue is purified by column chromatography on silica gel (eluant: dichloromethane/ethanol/ammonia=30:1).

Yield: 0.15 g (9.2% of theory), $C_{19}H_2SN_3O_2$ (M=327.43) Calc.: molecular peak (M+H)$^+$: 328. Found: molecular peak (M+H)$^+$: 328.

b. 2-(2-methyl-piperazin-1-yl)-quinoline

A solution of 0.15 g (0.458 mmol) of tert.butyl 3-methyl-4-quinolin-2-yl-piperazine-1-carboxylate in 1 ml of trifluoroacetic acid and 20 ml of dichloromethane is stirred for ten hours at ambient temperature. Then the solution is concentrated by evaporation, the residue is taken up in water and made alkaline with dilute sodium hydroxide solution. The aqueous phase is extracted with dichloromethane and the organic phase is dried over sodium sulphate.

Yield: 0.09 g (86.4% of theory), c. 9-{4-[3-methyl-4-quinolin-2-yl-piperazin-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-[2-methyl-piperazin-1-yl]-quinoline Yield: 0.02 g (8.8% of theory), Melting point: 50° C. $C_{34}H_{35}F_3N_4O$ (M=572.67) Calc.: molecular peak (M−H)$^-$: 571. Found: molecular peak (M−H)$^-$: 571.

EXAMPLE 41

9-[4-(trans-2,5-dimethyl-4-quinolin-2-yl-piperazin-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-(trans-2,5-dimethyl-piperazin-1-yl)-quinoline.

Yield: 0.1 g (24.2% of theory), $C_{35}H_{37}F_3N_4O$ (M=586.70) Calc.: molecular peak (M−H)$^-$: 585. Found: molecular peak (M−H)$^-$: 585.

EXAMPLE 42

9-[4-(cis-2,6-dimethyl-4-quinolin-2-yl-piperazin-1-yl)-butyl]-9H-fluorene-9-carboxylic acid-(2,2,2-trifluoro-ethyl)-amide a. 2-(cis-3,5-dimethyl-piperazin-1-yl)-quinoline Prepared analogously to Example 38 from cis-2,6-dimethyl-piperazine and 2-chloroquinoline.

Yield: 0.2 g (6.8% of theory), $C_{15}H_{19}N_3$ (M=241.33) Calc.: molecular peak (M+H)$^+$: 242. Found: molecular peak (M+H)$^+$: 242.

b. 9-[4-(cis-2,6-dimethyl-4-quinolin-2-yl-piperazin-1-yl)-butyl]-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 2-(cis-3,5-dimethyl-piperazin-1-yl)-quinoline.

Yield: 0.04 g (9.7% of theory), Melting point: 169° C. $C_{35}H_{37}F_3N_4O$ (M=586.70) Calc.: molecular peak (M+H)$^+$: 587. Found: molecular peak (M+H)$^+$: 587.

EXAMPLE 43

9-{4-[cis-2,6-dimethyl-4-(1-methyl-1H-benzimidazol-2-yl)-piperazin-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 2-(cis-3,5-dimethyl-piperazin-1-yl)-1-methyl-1H-benzimidazole.

Yield: 0.06 g (10.8% of theory), Melting point: 77° C. $C_{34}H_{38}F_3N_5O$ (M=589.71) Calc.: molecular peak (M+H)$^+$: 590. Found: molecular peak (M+H)$^+$: 590.

EXAMPLE 44

9-{4-[4-(5-chloro-quinolin-2-yl)-cis-2,6-dimethyl-piperazin-1-yl]-butyl}-9H-fluorene-9-carboxylic acid(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 5-chloro-2-(cis-3,5-dimethyl-piperazin-1-yl)-quinoline.

Yield: 0.22 g (50.3% of theory), Melting point: 199–201° C. $C_{35}H_{36}ClF_3N_4O$ (M=621.15) Calc.: molecular peak (M+H)$^+$: 621/623. Found: molecular peak (M+H)$^+$: 621/623.

EXAMPLE 45

9-[4-(4-benzothiazole-2-yl-cis-2,6-dimethyl-piperazin-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-(cis-3,5-dimethyl-piperazin-1-yl)-benzothiazole.

Yield: 0.28 g (67.1% of theory), Melting point: 163–165° C. $C_{33}H_{35}F_3N_4OS$ (M=592.73) Calc.: molecular peak (M+H)$^+$: 593. Found: molecular peak (M+H)$^+$: 593.

EXAMPLE 46

9-[4-(4-benzoxazol-2-yl-cis-2,6-dimethyl-piperazin-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-(cis-3,5-dimethyl-piperazin-1-yl)-benzoxazole.

Yield: 0.32 g (78.8% of theory), Melting point: 163–165° C. $C_{33}H_{35}F_3N_4O_2$ (M=576.66) Calc.: molecular peak (M+H)$^+$: 577. Found: molecular peak (M+H)$^+$: 577.

EXAMPLE 47

9-[4-(cis-2,6-dimethyl-4-quinazolin-2-yl-piperazin-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-(cis-3,5-dimethyl-piperazin-1-yl)-quinazoline.

Yield: 0.33 g (79.8% of theory), Melting point: 174° C. $C_{34}H_{36}F_3N_5O$ (M=587.69) Calc.: molecular peak (M+H)$^+$: 588. Found: molecular peak (M+H)$^+$: 588.

EXAMPLE 48

9-[4-(4-quinazolin-2-yl-[1.4]diazepan-1-yl)-butyl]-9H-fluorene-9-carboxylic acid-(2,2,2-trifluoro-ethyl)-amide a. 2-[1.4]diazepan-1-yl-quinazoline A reaction mixture of 2 g (12.1 mmol) of 2-chloroquinazoline and 3.65 g (36.45 mmol) of [1.4] diazepan is stirred for one hour at 140° C. The cooled reaction mixture is dissolved in dichloromethane/ethanol/ammonia. The product is purified by column chromatography on silica gel (eluant: dichloromethane/ethanol/ammonia=35:1:0.1).

Yield: 0.5 g (18% of theory), $C_{13}H_{16}N_4$ (M=228.29) Calc.: molecular peak (M+H)$^+$: 229. Found: molecular peak (M+H)$^+$: 229.

b. 9-[4-(4-quinazolin-2-yl-[1.4]diazepan-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-[1.4]diazepan-1-yl-quinazoline Yield: 0.4 g (14.9% of theory), Melting point: 76° C. $C_{33}H_{34}F_3N_5O$ (M=573.66) Calc.: molecular peak (M+H)$^+$: 574. Found: molecular peak (M+H)$^+$: 574.

EXAMPLE 49

9-[4-(4-quinolin-2-yl-[1.4]diazepan-1-yl)-butyl]-9H-fluorene-9-carboxylic acid-(2,2,2-trifluoro-ethyl)-amide Prepared analogously to Example 2b from 9-(4-bromo-butyl)-9H-fluorene-9-carboxylic acid-(2,2,2-trifluoro-ethyl)-amide and 2-[1.4]diazepan-1-yl-quinoline Yield: 0.11 g (20.5% of theory), $C_{34}H_{35}F_3N_4O$ (M=572.67) Calc.: molecular peak (M+H)$^+$: 573. Found: molecular peak (M+H)$^+$: 573.

EXAMPLE 50

9-{4-[4-(6-chloro-quinolin-2-yl)-[1.4] diazepan-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 6-chloro-2-[1.4]diazepan-1-yl-quinoline Yield: 0.21 g (49% of theory), Melting point: 62° C. $C_{34}H_{34}ClF_3N_4O$ (M=607.12) Calc.: molecular peak (M+H)$^+$: 607/609. Found: molecular peak (M+H)$^+$: 607/609.

EXAMPLE 51

9-{4-[4-(6-chloro-benzothiazol-2-yl)-[1.4]diazepan-1-yl]-butyl}-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 6-chloro-2-[1.4]diazepan-1-yl-benzothiazole.

Yield: 0.036 g (16% of theory), Melting point: 80° C. $C_{32}H_{32}ClF_3N_4OS$ (M=613.15) Calc.: molecular peak (M)$^+$: 612/614. Found: molecular peak (M)$^+$: 612/614.

EXAMPLE 52

9-[4-(4-benzothiazol-2-yl-[1.4]diazepan-1-yl)-butyl]-9H-fluorene-9-carboxylic acid-(2,2,2-trifluoro-ethyl)-amide Prepared analogously to Example 1 from 9-(4-bromo-butyl)-9H-fluorene-9-carboxylic acid-(2,2,2-trifluoro-ethyl)-amide and 2-[1.4] diazepan-1-yl-benzothiazole.

Yield: 0.4 g (53.7% of theory), Melting point: 136° C. $C_{32}H_{33}F_3N_4OS$ (M=578.70) Calc.: molecular peak (M+H)$^+$: 579. Found: molecular peak (M+H)$^+$: 579.

EXAMPLE 53

9-[4-(4-quinolin-2-yl-piperazin-1-yl)-butyl]-9H-fluorene-9-carboxylic acid-4-fluoro-benzylamide a. 9-(4-bromo-butyl)-9H-fluorene-9-carboxylic acid-4-fluoro-benzylamide Prepared analogously to Example 1 from 4-fluoro-benzylamine and 9-(4-bromo-butyl)-9H-fluorene-9-carboxylic acid chloride.

Yield: 1.8 g (68.9% of theory), $C_{25}H_{23}BrFNO$ (M=452.37) Calc.: molecular peak (M−H)$^−$: 450/452. Found: molecular peak (M−H)$^−$: 450/452.

b. 9-[4-(4-quinolin-2-yl-piperazin-1-yl)-butyl]-9H-fluorene-9-carboxylic acid-4-fluoro-benzylamide Prepared analogously to Example 1 from 9-(4-bromo-butyl)-9H-fluorene-9-carboxylic acid-4-fluoro-benzylamide and 2-piperazin-1-yl-quinoline.

Yield: 0.36 g (92.9% of theory), Melting point: 58° C. $C_{38}H_{37}FN_4O$ (M=584.74) Calc.: molecular peak (M+H)$^+$: 585. Found: molecular peak (M+H)$^+$: 585.

EXAMPLE 54

9-{4-[4-(5-chloro-quinolin-2-yl)-piperazin-1-yl]-butyl}-9H-fluorene-9-carboxylic acid-4-fluoro-benzylamide Prepared analogously to Example 2 from 9-(4-bromo-butyl)-9H-fluorene-9-carboxylic acid-4-fluoro-benzylamide and 5-chloro-2-piperazin-1-yl-quinoline.

Yield: 0.18 g (65.8% of theory), Melting point: 140° C. $C_{37}H_{36}ClFN_4O$ (M=619.18) Calc.: molecular peak (M+H)$^+$: 619/620. Found: molecular peak (M+H)$^+$: 619/620.

EXAMPLE 55

9-{4-[4-(8-chloro-quinolin-2-yl)-piperazin-1-yl]-butyl}-9H-fluorene-9-carboxylic acid-4-fluoro-benzylamide Prepared analogously to Example 2 from 9-(4-bromo-butyl)-9H-fluorene-9-carboxylic acid-4-fluoro-benzylamide and 8-chloro-2-piperazin-1-yl-quinoline.

Yield: 0.04 g (11.7% of theory), Melting point: 66° C. $C_{38}H_{36}ClFN_4O$ (M=619.18) Calc.: molecular peak (M+H)$^+$: 619/621. Found: molecular peak (M+H)$^+$: 619/621.

EXAMPLE 57

9-[4-(4-quinoxalin-2-yl-piperazin-1-yl)-butyl]-9H-fluorene-9-carboxylic acid-4-fluoro-benzylamide Prepared analogously to Example 1 from 9-(4-bromo-butyl)-9H-fluorene-9-carboxylic acid-4-fluoro-benzylamide and 2-piperazin-1-yl-quinoxaline.

Yield: 0.21 g (54.1% of theory), Melting point: 160° C. $C_{37}H_{36}FN_5O$ (M=585.73) Calc.: molecular peak (M−H)$^−$: 584. Found: molecular peak (M−H)$^−$: 584.

EXAMPLE 58

9-[4-(4-quinazolin-2-yl-piperazin-1-yl)-butyl]-9H-fluorene-9-carboxylic acid-4-fluoro-benzylamide Prepared analogously to Example 1 from 9-(4-bromo-butyl)-9H-fluorene-9-carboxylic acid-4-fluoro-benzylamide and 2-piperazin-1-yl-quinazoline.

Yield: 0.26 g (67% of theory), Melting point: 160° C. $C_{37}H_{36}FN_5O$ (M=585.73) Calc.: molecular peak (M+H)$^+$: 586. Found: molecular peak (M+H)$^+$: 586.

EXAMPLE 59

9-[4-(4-benzothiazol-2-yl-piperazin-1-yl)-butyl]-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 2-piperazin-1-yl-benzothiazole.

Yield: 0.16 g (40.8% of theory), Melting point: 160° C. $C_{36}H_{35}FN_4OS$ (M=590.76) Calc.: molecular peak (M+H)$^+$: 591. Found: molecular peak (M+H)$^+$: 591.

EXAMPLE 60

9-{4-[4-(1-methyl-1H-benzimidazol-2-yl)-piperazin-1-yl]-butyl}-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 1-methyl-2-piperazin-1-yl-1H-benzimidazole.

Yield: 0.13 g (33.4% of theory), Melting point: 55° C. $C_{37}H_{38}FN_5O$ (M=587.74) Calc.: molecular peak (M+H)$^+$: 588. Found: molecular peak (M+H)$^+$: 588.

EXAMPLE 61

9-{4-[4-(1-ethyl-1H-benzimidazol-2-yl)-piperazin-1-yl]-butyl}-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 1-ethyl-2-piperazin-1-yl-1H-benzimidazole.

Yield: 0.37 g (92.7% of theory), Melting point: 166° C. $C_{38}H_{40}FN_5O$ (M=601.77) Calc.: molecular peak (M–H)$^-$: 600. Found: molecular peak (M–H)$^-$: 600.

EXAMPLE 62

9-{4-[4-(6-fluoro-1-methyl-1H-benzimidazol-2-yl)-piperazin-1-yl]-butyl}-9H-fluorene-9-carboxylic acid-4-fluoro-benzylamide Prepared analogously to Example 1e from 9-(4-bromobutyl)-9H-fluorene-9-carboxylic acid-4-fluoro-benzylamide and 6-fluoro-1-methyl-2-piperazin-1-yl-1H-benzimidazole.

Yield: 0.13 g (32.4% of theory), Melting point: 43° C. $C_{37}H_{38}F_2N_5O$ (M=605.73) Calc.: molecular peak (M+H)$^+$: 606. Found: molecular peak (M+H)$^+$: 606.

EXAMPLE 63

9-{4-[4-(3-methyl-3H-imidazo[4,5]-pyridin-2-yl)-piperazin-1-yl]-butyl}-9H-fluorene-9-carboxylic acid-4-fluoro-benzylamide Prepared analogously to Example 1e from 9-(4-bromobutyl)-9H-fluorene-9-carboxylic acid-4-fluoro-benzylamide and 3-methyl-2-piperazin-1-yl-3H-imidazo[4,5]1-pyridine.

Yield: 0.3 g (76.9% of theory), Melting point: 153° C. $C_{36}H_{37}FN_6O$ (M=588.73) Calc.: molecular peak (M+H)$^+$: 589. Found: molecular peak (M+H)$^+$: 589.

EXAMPLE 64

9-{4-[(S)-2-methyl-4-quinolin-2-yl-piperazin-1-yl]-butyl}-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 2-[(S)-3-methyl-piperazin-1-yl]-quinoline Yield: 0.1 g (13.5% of theory), Melting point: 124° C. $C_{39}H_{39}FN_4O$ (M=598.77) Calc.: molecular peak (M–H)$^-$: 597. Found: molecular peak (M–H)$^-$: 597.

EXAMPLE 65

9-[4-(cis-2,6-dimethyl-4-quinolin-2-yl-piperazin-1-yl) butyl]-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 2-(cis-3,5-dimethyl-piperazin-1-yl)-quinoline Yield: 0.08 g (14.8% of theory), Melting point: 62° C. $C_{40}H_{41}FN_4O$ (M=612.79) Calc.: molecular peak (M+H)$^+$: 613. Found: molecular peak (M+H)$^+$: 613.

EXAMPLE 66

9-{4-[4-(5-chloro-quinolin-2-yl)-cis-2,6-dimethyl-piperazin-1-yl]-butyl}-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 5-chloro-2-(cis-3,5-dimethyl-piperazin-1-yl)-quinoline.

Yield: 0.2 g (46.6% of theory), Melting point: 136–137° C. $C_{40}H_{40}ClFN_4O$ (M=647.24) Calc.: molecular peak (M+H)$^+$: 647/649. Found: molecular peak (M+H)$^+$: 647/649.

EXAMPLE 67

9-[4-(cis-2,6-dimethyl-4-quinazoline-2-yl-piperazin-1-yl)-butyl]-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 2-(cis-3,5-dimethyl-piperazin-1-yl)-quinazoline.

Yield: 0.19 g (46.7% of theory), Melting point: 172° C. $C_{39}H_{40}FN_5O$ (M=613.78) Calc.: molecular peak (M–H)$^-$: 612. Found: molecular peak (M–H)$^-$: 612.

EXAMPLE 68

9-{4-[cis-2,6-dimethyl-4-(1-methyl-1H-benzimidazol-2-yl)-piperazin-1-yl]-butyl}-9H-fluorene-9-carboxylic acid-4-fluoro-benzylamide Prepared analogously to Example 42 from 9-(4-bromobutyl)-9H-fluorene-9-carboxylic acid-4-fluoro-benzylamide and 2-(cis-3,5-dimethyl-piperazin-1-yl)-1-methyl-1H-benzimidazole.

Yield: 0.12 g (29.4% of theory), $C_{39}H_{42}FN_5O$ (M=615.80) Calc.: molecular peak (M+H)$^+$: 616. Found: molecular peak (M+H)$^+$: 616.

EXAMPLE 69

9-[4-(4-benzoxazol-2-yl-cis-2,6-dimethyl-piperazin-1-yl)-butyl]-9H-fluorene-9-carboxylic acid-4-fluoro-benzylamide Prepared analogously to Example 1 from 9-(4-bromobutyl)-9H-fluorene-9-carboxylic acid-4-fluoro-benzylamide and 2-(cis-3,5-dimethyl-piperazin-1-yl)-benzoxazole.

Yield: 0.08 g (20% of theory), Melting point: 153° C. $C_{38}H_{39}FN_4O_2$ (M=602.75) Calc.: molecular peak (M–H)$^-$: 601. Found: molecular peak (M–H)$^-$: 601.

EXAMPLE 70

9-[4-(4-benzothiazol-2-yl-cis-2,6-dimethyl-piperazin-1-yl)-butyl]-9H-fluorene-9-carboxylic acid-4-fluoro-benzylamide Prepared analogously to Example 1 from 9-(4-bromo-butyl)-9H-fluorene-9-carboxylic acid-4-fluoro-benzylamide and 2-(cis-3,5-dimethyl-piperazin-1-yl)-benzothiazole.

Yield: 0.17 g (41.4% of theory), Melting point: 171° C. $C_{38}H_{39}FN_4OS$ (M=618.82) Calc.: molecular peak $(M+H)^+$: 619. Found: molecular peak $(M+H)^+$: 619.

EXAMPLE 71

9-[4-(4-benzothiazol-2-yl-[1.4]diazepan-1-yl)-butyl]-9H-fluorene-9-carboxylic acid-4-fluoro-benzylamide Prepared analogously to Example 1 from 9-(4-bromo-butyl)-9H-fluorene-9-carboxylic acid-4-fluoro-benzylamide and 2-[1.4]diazepan-1-yl-benzothiazole.

Yield: 0.13 g (25.1% of theory), Melting point: 58° C. $C_{37}H_{37}FN_4OS$ (M=604.79) Calc.: molecular peak $(M+H)^+$: 605. Found: molecular peak $(M+H)^+$: 605.

EXAMPLE 72

9-[4-(4-quinolin-2-yl-piperazin-1-yl)-butyl]-9H-fluorene-9-carboxylic acid-4-methoxy-benzylamide a. 9-(4-bromo-butyl)-9H-fluorene-9-carboxylic acid-4-methoxy-benzylamide Prepared analogously to Example 1 from 4-methoxybenzylamine and 9-(4-bromo-butyl)-9H-fluorene-9-carboxylic acid chloride.

Yield: 2.11 g (66.1% of theory), Melting point: 78–80° C. $C_{26}H_{26}BrNO_2$ (M=464.40) Calc.: molecular peak $(M-H)^-$: 462/464. Found: molecular peak $(M-H)^-$: 462/464.

b. 9-[4-(4-quinolin-2-yl-piperazin-1-yl)-butyl]-9H-fluorene-9-carboxylic acid-4-methoxy-benzylamide Prepared analogously to Example 2 from 9-(4-bromo-butyl)-9H-fluorene-9-carboxylic acid-4-methoxy-benzylamide and 2-piperazin-1-yl-quinoline.

Yield: 0.26 g (67.4% of theory), $C_{39}H_{40}N_4O_2$ (M=596.77) Calc.: molecular peak $(M+H)^+$: 597. Found: molecular peak $(M+H)^+$: 597.

EXAMPLE 73

9-{4-[4-(5-chloro-quinolin-2-yl)-piperazin-1-yl]-butyl}-9H-fluorene-9-carboxylic acid-4-methoxy-benzylamide Prepared analogously to Example 2 from 9-(4-bromo-butyl)-9H-fluorene-9-carboxylic acid-4-methoxy-benzylamide and 5-chloro-2-piperazin-1-yl-quinoline.

Yield: 0.05 g (18.4% of theory), Melting point: 135–136° C. $C_{39}H_{39}ClN_4O_2$ (M=631.22) Calc.: molecular peak $(M-H)^-$: 629/631. Found: molecular peak $(M-H)^-$: 629/631.

EXAMPLE 74

9-[4-(4-quinazolin-2-yl-piperazin-1-yl)-butyl]-9H-fluorene-9-carboxylic acid-4-methoxy-benzylamide Prepared analogously to Example 1 from 9-(4-bromo-butyl)-9H-fluorene-9-carboxylic acid-4-methoxy-benzylamide and 2-piperazin-1-yl-quinazoline.

Yield: 0.06 g (23.3% of theory), Melting point: 143–144° C. $C_{38}H_{39}N_5O_2$ (M=597.76) Calc.: molecular peak $(M+H)^+$: 598. Found: molecular peak $(M+H)^+$: 598.

EXAMPLE 75

9-{4-[4-(1-methyl-1H-benzimidazol-2-yl)-piperazin-1-yl]-butyl}-9H-fluorene-9-carboxylic acid-4-methoxy-benzylamide Prepared analogously to Example 1e from 9-(4-bromo-butyl)-9H-fluorene-9-carboxylic acid-4-methoxy-benzylamide and 1-methyl-2-piperazin-1-yl-1H-benzimidazole.

Yield: 0.2 g (77.4% of theory), $C_{38}H_{41}N_5O_2$ (M=599.78) Calc.: molecular peak $(M+H)^+$: 600. Found: molecular peak $(M+H)^+$: 600.

EXAMPLE 76

9-[4-(4-benzothiazol-2-yl-piperazin-1-yl)-butyl]-9H-fluorene-9-carboxylic acid-4-methoxy-benzylamide Prepared analogously to Example 1e from 9-(4-bromo-butyl)-9H-fluorene-9-carboxylic acid-4-methoxy-benzylamide and 2-piperazin-1-yl-benzothiazole.

Yield: 0.19 g (73.1% of theory), Melting point: 145° C. $C_{37}H_{38}N_4O_2S$ (M=602.80) Calc.: molecular peak $(M+H)^+$: 603. Found: molecular peak $(M+H)^+$: 603.

EXAMPLE 77

9-[4-(cis-2,6-dimethyl-4-quinolin-2-yl-piperazin-1-yl)-butyl]-9H-fluorene-9-carboxylic acid-4-methoxy-benzylamide Prepared analogously to Example 1 from 9-(4-bromo-butyl)-9H-fluorene-9-carboxylic acid-4-methoxy-benzylamide and 2-(cis-3,5-dimethyl-piperazin-1-yl)-quinoline Yield: 0.08 g (29.7% of theory), $C_{41}H_{44}N_4O_2$ (M=624.83) Calc.: molecular peak $(M+H)^+$: 625. Found: molecular peak $(M+H)^+$: 625.

EXAMPLE 78

9-{4-[4-(5-chloro-quinolin-2-yl)-cis-2,6-dimethyl-piperazin-1-yl]-butyl}-9H-fluorene-9-carboxylic acid-4-methoxy-benzylamide Prepared analogously to Example 2 from 9-(4-bromo-butyl)-9H-fluorene-9-carboxylic acid-4-methoxy-benzylamide and 5-chloro-2-(cis-3,5-dimethyl-piperazin-1-yl)-quinoline.

Yield: 0.02 g (7% of theory), $C_{41}H_{43}ClN_4O_2$ (M=659.27) Calc.: molecular peak $(M+H)^+$: 659/661. Found: molecular peak $(M+H)^+$: 659/661.

EXAMPLE 79

9-[4-(4-benzothiazol-2-yl-[1.4]diazepan-1-yl)-butyl]-9H-fluorene-9-carboxylic acid-4-methoxy-benzylamide Prepared analogously to Example 1 from 9-(4-bromo-butyl)-9H-fluorene-9-carboxylic acid-4-methoxy-benzylamide and 2-[1.4]diazepan-1-yl-benzothiazole.

Yield: 0.15 g (28.4% of theory), Melting point: 58° C. $C_{38}H_{40}N_4O_2S$ (M=616.83) Calc.: molecular peak $(M+H)^+$: 617. Found: molecular peak $(M+H)^+$: 617.

EXAMPLE 80

9-[4-(4-quinolin-2-yl-piperazin-1-yl)-butyl]-9H-fluorene-9-carboxylic acid-2-methoxy-benzylamide a. 9-(4-bromo-butyl)-9H-fluorene-9-carboxylic acid-4-methoxy-benzylamide Prepared analogously to Example 1 from 2-methoxybenzylamine and 9-(4-bromo-butyl)-9H-fluorene-9-carboxylic acid chloride.

Yield: 1.2 g (37.6% of theory), Melting point: 100–102° C. $C_{26}H_{26}BrNO_2$ (M=464.40) Calc.: molecular peak $(M+H)^+$: 464/466. Found: molecular peak $(M+H)^+$: 464/466.

b. 9-[4-(4-quinolin-2-yl-piperazin-1-yl)-butyl]-9H-fluorene-9-carboxylic acid-2-methoxy-benzylamide Prepared analogously to Example 2 from 9-(4-bromo-butyl)-9H-fluorene-9-carboxylic acid-2-methoxy-benzylamide and 2-piperazin-1-yl-quinoline.

Yield: 0.25 g (64.8% of theory), $C_{39}H_{40}N_4O_2$ (M=596.77) Calc.: molecular peak $(M-H)^-$: 595. Found: molecular peak $(M-H)^-$: 595.

EXAMPLE 81

9-[4-(4-quinolin-2-yl-piperazin-1-yl)-butyl]-9H-fluorene-9-carboxylic acid-3-methoxy-benzylamide a. 9-(4-bromo-butyl)-9H-fluorene-9-carboxylic acid-3-methoxy-benzylamide Prepared analogously to Example 1 from 3-methoxybenzylamine and 9-(4-bromo-butyl)-9H-fluorene-9-carboxylic acid chloride.

Yield: 2.3 g (72% of theory), Melting point: 69–71° C. $C_{26}H_{26}BrNO_2$ (M=464.40) Calc.: molecular peak $(M-H)^-$: 462/464. Found: molecular peak $(M-H)^-$: 462/464.

b. 9-[4-(4-quinolin-2-yl-piperazin-1-yl)-butyl]-9H-fluorene-9-carboxylic acid-3-methoxy-benzylamide Prepared analogously to Example 2 from 9-(4-bromo-butyl)-9H-fluorene-9-carboxylic acid-3-methoxy-benzylamide and 2-piperazin-1-yl-quinoline.

Yield: 0.26 g (67.4% of theory), Melting point: 114–116° C. $C_{39}H_{40}N_4O_2$ (M=596.77) Calc.: molecular peak $(M-H)^-$: 595. Found: molecular peak $(M-H)^-$: 595.

EXAMPLE 82

9-[4-(4-quinolin-2-yl-piperazin-1-yl)-butyl]-9H-fluorene-9-carboxylic acid-2,4-dimethoxy-benzylamide a. 9-(4-bromo-butyl)-9H-fluorene-9-carboxylic acid-2,4-dimethoxy-benzylamide Prepared analogously to Example 1 from 2,4-dimethoxybenzylamine and 9-(4-bromo-butyl)-9H-fluorene-9-carboxylic acid chloride.

Yield: 2.7 g (90.3% of theory), $C_{27}H_{28}BrNO_3$ (M=494.43) Calc.: molecular peak $(M+H)^+$: 494/496. Found: molecular peak $(M+H)^+$: 494/496.

b. 9-[4-(4-quinolin-2-yl-piperazin-1-yl)-butyl]-9H-fluorene-9-carboxylic acid-2,4-dimethoxy-benzylamide Prepared analogously to Example 1 from 9-(4-bromo-butyl)-9H-fluorene-9-carboxylic acid-2,4-dimethoxy-benzylamide and 2-piperazin-1-yl-quinoline.

Yield: 0.31 g (62% of theory), Melting point: 44° C. $C_{40}H_{42}N_4O_3$ (M=626.80) Calc.: molecular peak $(M+H)^+$: 627. Found: molecular peak $(M+H)^+$: 627.

EXAMPLE 83

9-[4-(4-quinolin-2-yl-piperazin-1-yl)-butyl]-9H-fluorene-9-carboxylic acid-3,4-dimethoxy-benzylamide a. 9-(4-bromo-butyl)-9H-fluorene-9-carboxylic acid-3,4-dimethoxy-benzylamide Prepared analogously to Example 1 from 3,4-dimethoxybenzylamine and 9-(4-bromo-butyl)-9H-fluorene-9-carboxylic acid chloride.

Yield: 0.78 g (77.9% of theory), $C_{27}H_{28}BrNO_3$ (M=494.43) Calc.: molecular peak $(M+Na)^+$: 516/518. Found: molecular peak $(M+Na)^+$: 516/518.

b. 9-[4-(4-quinolin-2-yl-piperazin-1-yl)-butyl]-9H-fluorene-9-carboxylic acid-3,4-dimethoxy-benzylamide Prepared analogously to Example 1 from 9-(4-bromo-butyl)-9H-fluorene-9-carboxylic acid-3,4-dimethoxy-benzylamide and 2-piperazin-1-yl-quinoline.

Yield: 0.25 g (50.9% of theory), Melting point: 118° C. $C_{40}H_{42}N_4O_3$ (M=626.80) Calc.: molecular peak $(M+H)^+$: 627. Found: molecular peak $(M+H)^+$: 627.

EXAMPLE 84

9-[4-(4-quinolin-2-yl-piperazin-1-yl)-butyl]-9H-fluorene-9-carboxylic acid-2,4-difluoro-benzylamide a. 9-(4-bromo-butyl)-9H-fluorene-9-carboxylic acid-2,4-difluoro-benzylamide Prepared analogously to Example 1 from 2,4-difluorbenzylamine and 9-(4-bromo-butyl)-9H-fluorene-9-carboxylic acid chloride.

Yield: 3.2 g (82.5% of theory), Melting point: 90–92° C. $C_{25}H_{22}BrF_2NO$ (M=470.36) Calc.: molecular peak $(M-H)^-$: 468/470. Found: molecular peak $(M-H)^-$: 468/470.

b. 9-[4-(4-quinolin-2-yl-piperazin-1-yl)-butyl]-9H-fluorene-9-carboxylic acid-2,4-difluoro-benzylamide Prepared analogously to Example 1 from 9-(4-bromo-butyl)-9H-fluorene-9-carboxylic acid-2,4-difluoro-benzylamide and 2-piperazin-1-yl-quinoline.

Yield: 0.31 g (80.6% of theory), Melting point: 116–118° C. $C_{38}H_{36}F_2N_4O$ (M=602.73) Calc.: molecular peak $(M+H)^+$: 603. Found: molecular peak $(M+H)^+$: 603.

EXAMPLE 85

9-[4-(4-quinolin-2-yl-piperazin-1-yl)-butyl]-9H-fluorene-9-carboxylic acid-3,4-difluoro-benzylamide a. 9-(4-bromo-butyl)-9H-fluorene-9-carboxylic acid-3,4-difluoro-benzylamide Prepared analogously to Example 1 from 3,4-difluorobenzylamine and 9-(4-bromo-butyl)-9H-fluorene-9-carboxylic acid chloride.

Yield: 2.1 g (64.9% of theory), Melting point: 132–134° C. $C_{25}H_{22}BrF_2NO$ (M=470.36) Calc.: molecular peak $(M-H)^-$: 468/470. Found: molecular peak $(M-H)^-$: 468/470.

b. 9-[4-(4-quinolin-2-yl-piperazin-1-yl)-butyl]-9H-fluorene-9-carboxylic acid-3,4-difluoro-benzylamide Prepared analogously to Example 2 from 9-(4-bromo-butyl)-9H-fluorene-9-carboxylic acid-3,4-difluoro-benzylamide and 2-piperazin-1-yl-quinoline.

Yield: 0.19 g (49.4% of theory), Melting point: 141–143° C. $C_{38}H_{36}F_2N_4O$ (M=602.73) Calc.: molecular peak $(M-H)^-$: 601. Found: molecular peak $(M-H)^-$: 601.

EXAMPLE 86

9-[4-(4-quinolin-2-yl-piperazin-1-yl)-butyl]-9H-fluorene-9-carboxylic acid-(2,2,3,3,3-pentafluoro-propyl)-amide a. 9-(4-bromo-butyl)-9H-fluorene-9-carboxylic acid-(2,2,3,3,3-pentafluoro-propyl)-amide Prepared analogously to Example 1 from 2,2,3,3,3-pentafluoro-propylamine and 9-(4-bromo-butyl)-9H-fluorene-9-carboxylic acid chloride.

Yield: 1.4 g (16% of theory), $C_{21}H_{19}BrF_5NO$ (M=476.28) Calc.: molecular peak $(M–H)^−$: 474/476. Found: molecular peak $(M–H)^−$: 474/476.

b. 9-[4-(4-quinolin-2-yl-piperazin-1-yl)-butyl]-9H-fluorene-9-carboxylic acid-(2,2,3,3,3-pentafluoro-propyl)-amide Prepared analogously to Example 1 from 9-(4-bromo-butyl)-9H-fluorene-9-carboxylic acid-(2,2,3,3,3-pentafluoro-propyl)-amide and 2-piperazin-1-yl-quinoline.

Yield: 0.13 g (50.9% of theory), Melting point: 120° C. $C_{34}H_{33}F_5N_4O$ (M=608.66) Calc.: molecular peak $(M–H)^−$: 607. Found: molecular peak $(M–H)^−$: 607.

EXAMPLE 87

9-{4-[4-(1-methyl-1H-benzimidazol-2-yl)-piperazin-1-yl]-butyl}-9H-fluorene-9-carboxylic acid-(2,2,3,3,3-pentafluoro-propyl)-amide Prepared analogously to Example 1 from 9-(4-bromo-butyl)-9H-fluorene-9-carboxylic acid-(2,2,3,3,3-pentafluoro-propyl)-amide and 1-methyl-2-piperazin-1-yl-1H-benzimidazole.

Yield: 0.1 g (38.9% of theory), Melting point: 120° C. $C_{33}H_{34}F_5N_5O$ (M=611.66) Calc.: molecular peak $(M–H)^−$: 610. Found: molecular peak $(M–H)^−$: 610.

EXAMPLE 88

9-[4-(4-quinolin-2-yl-piperazin-1-yl)-butyl]-9H-fluorene-9-carboxylic acid-(pyridin-4-ylmethyl)-amide a. 9-(4-bromo-butyl)-9H-fluorene-9-carboxylic acid-(pyridin-4-ylmethyl)-amide Prepared analogously to Example 1 from 4-(aminomethyl)-pyridine and 9-(4-bromo-butyl)-9H-fluorene-9-carboxylic acid chloride.

Yield: 1.9 g (63.5% of theory), $C_{24}H_{23}BrN_2O$ (M=435.36) Calc.: molecular peak $(M–H)^−$: 433/435. Found: molecular peak $(M–H)^−$: 433/435.

b. 9-[4-(4-quinolin-2-yl-piperazin-1-yl)-butyl]-9H-fluorene-9-carboxylic acid-(pyridin-4-ylmethyl)-amide Prepared analogously to Example 2 from 9-(4-bromo-butyl)-9H-fluorene-9-carboxylic acid-(pyridin-4-ylmethyl)-amide and 2-piperazin-1-yl-quinoline.

Yield: 0.23 g (58.8% of theory), Melting point: 166–168° C. $C_{37}H_{37}N_5O$ (M=567.74) Calc.: molecular peak $(M+H)^+$: 568. Found: molecular peak $(M+H)^+$: 568.

EXAMPLE 89

9-[4-(4-quinolin-2-yl-piperazin-1-yl)-butyl]-9H-fluorene-9-carboxylic acid-(pyridin-2-ylmethyl)-amide a. 9-(4-bromo-butyl)-9H-fluorene-9-carboxylic acid-(pyridin-2-ylmethyl)-amide Prepared analogously to Example 1 from 2-(aminomethyl)-pyridine and 9-(4-bromo-butyl)-9H-fluorene-9-carboxylic acid chloride.

Yield: 0.2 g (6.7% of theory), $C_{24}H_{23}BrN_2O$ (M=435.36) Calc.: molecular peak $(M–H)^−$: 433/435. Found: molecular peak $(M–H)^−$: 433/435.

b. 9-[4-(4-quinolin-2-yl-piperazin-1-yl)-butyl]-9H-fluorene-9-carboxylic acid-(pyridin-2-ylmethyl)-amide Prepared analogously to Example 1 from 9-(4-bromo-butyl)-9H-fluorene-9-carboxylic acid-(pyridin-2-ylmethyl)-amide and 2-piperazin-1-yl-quinoline.

Yield: 0.22 g (88.9% of theory), $C_{37}H_{37}N_5O$ (M=567.74) Calc.: molecular peak $(M+H)^+$: 568. Found: molecular peak $(M+H)^+$: 568.

EXAMPLE 90

9-[4-(4-quinolin-2-yl-piperazin-1-yl)-butyl]-9H-fluorene-9-carboxylic acid-(thiophen-2-ylmethyl)-amide a. 9-(4-bromo-butyl)-9H-fluorene-9-carboxylic acid-(thiophen-2-ylmethyl)-amide Prepared analogously to Example 1 from 2-(aminomethyl)-thiophene and 9-(4-bromo-butyl)-9H-fluorene-9-carboxylic acid chloride.

Yield: 2.6 g (86.6% of theory), $C_{23}H_{22}BrNOS$ (M=440.40) Calc.: molecular peak $(M–H)^−$: 438/440. Found: molecular peak $(M–H)^−$: 438/440.

b. 9-[4-(4-quinolin-2-yl-piperazin-1-yl)-butyl]-9H-fluorene-9-carboxylic acid-(thiophen-2-ylmethyl)-amide Prepared analogously to Example 1 from 9-(4-bromo-butyl)-9H-fluorene-9-carboxylic acid-(thiophen-2-ylmethyl)-amide and 2-piperazin-1-yl-quinoline.

Yield: 0.43 g (86.3% of theory), Melting point: 45–50° C. $C_{36}H_{36}N_4OS$ (M=572.77) Calc.: molecular peak $(M+H)^+$: 573. Found: molecular peak $(M+H)^+$: 573.

EXAMPLE 91

9-{4-[4-(1-methyl-1H-benzimidazol-2-yl)-piperazin-1-yl]-butyl}-9H-fluorene-9-carboxylic acid propylamide 9-{4-[4-(1-methyl-1H-benzimidazol-2-yl)-piperazin-1-yl]-butyl}-9H-fluorene-9-carboxylic acid propylamide Prepared analogously to Example 1 from 9-(4-bromo-butyl)-9H-fluorene-9-carboxylic acid-propylamide and 1-methyl-2-piperazin-1-yl-1H-benzimidazole.

Yield: 0.21 g (51.8% of theory), Melting point: 126° C. $C_{33}H_{39}N_5O$ (M=521.71) Calc.: molecular peak $(M+H)^+$: 522. Found: molecular peak $(M+H)^+$: 522.

EXAMPLE 92

9-[4-(4-quinolin-2-yl-piperazin-1-yl)-butyl]-9H-fluorene-9-carboxylic acid-(phenethyl)-amide a. 9-(4-bromo-butyl)-9H-fluorene-9-carboxylic acid-(phenethyl)-amide Prepared analogously to Example 1 from phenethylamine and 9-(4-bromo-butyl)-9H-fluorene-9-carboxylic acid chloride.

Yield: 2.08 g (67.5% of theory), Melting point: 83° C. $C_{23}H_{22}BrNOS$ (M=448.40) Calc.: molecular peak $(M+H)^+$: 448/450. Found: molecular peak $(M+H)^+$: 448/450.

b. 9-[4-(4-quinolin-2-yl-piperazin-1-yl)-butyl]-9H-fluorene-9-carboxylic acid-(phenethyl)-amide Prepared analogously to Example 2 from 9-(4-bromo-butyl)-9H-fluorene-9-carboxylic acid-(phenethyl)-amide and 2-piperazin-1-yl-quinoline.

Yield: 0.11 g (28.3% of theory), Melting point: 55–57° C. $C_{39}H_{40}N_4O$ (M=580.78) Calc.: molecular peak $(M+H)^+$: 581. Found: molecular peak $(M+H)^+$: 581.

EXAMPLE 93

9-[4-(4-quinolin-2-yl-piperazin-1-yl)-butyl]-9H-fluorene-9-carboxylic acid-(3-methoxy-propyl)-amide a. 9-(4-bromo-butyl)-9H-fluorene-9-carboxylic acid-(3-methoxy-propyl)-amide Prepared analogously to Example 1 from 3-methoxy-propylamine and 9-(4-bromo-butyl)-9H-fluorene-9-carboxylic acid chloride.

Yield: 2.32 g (77.9% of theory), $C_{22}H_{21}BrNO_2$ (M=416.36) Calc.: molecular peak (M+Na)$^+$: 438/440. Found: molecular peak (M+Na)$^+$: 438/440.

b. 9-[4-(4-quinolin-2-yl-piperazin-1-yl)-butyl]-9H-fluorene-9-carboxylic acid-(3-methoxy-propyl)-amide Prepared analogously to Example 1 from 9-(4-bromo-butyl)-9H-fluorene-9-carboxylic acid-(3-methoxy-propyl)-amide and 2-piperazin-1-yl-quinoline.

Yield: 0.38 g (75.3% of theory), Melting point: 87° C. $C_{35}H_{40}N_4O_2$ (M=548.73) Calc.: molecular peak (M+H)$^+$: 549. Found: molecular peak (M+H)$^+$: 549.

EXAMPLE 94

9-[4-(4-quinolin-2-yl-piperazin-1-yl)-butyl]-9H-fluorene-9-carboxylic acid-(2-methoxycarbonyl-ethyl)-amide a. 9-(4-bromo-butyl)-9H-fluorene-9-carboxylic acid-(2-methoxycarbonyl-ethyl)-amide Prepared analogously to Example 1 from beta-alanine-methyl ester and 9-(4-bromo-butyl)-9H-fluorene-9-carboxylic acid chloride.

Yield: 1.5 g (50.7% of theory), Melting point: 83° C. $C_{22}H_{24}BrNO_3$ (M=430.34) Calc.: molecular peak (M+H)$^+$: 430/432. Found: molecular peak (M+H)$^+$: 430/432.

b. 9-[4-(4-quinolin-2-yl-piperazin-1-yl)-butyl]-9H-fluorene-9-carboxylic acid-(2-methoxycarbonyl-ethyl)-amide Prepared analogously to Example 2 from 9-(4-bromo-butyl)-9H-fluorene-9-carboxylic acid-(2-methoxycarbonyl-ethyl)-amide and 2-piperazin-1-yl-quinoline.

Yield: 0.1 g (25.5% of theory), Melting point: 110–112° C. $C_{35}H_{38}N_4O_3$ (M=562.71) Calc.: molecular peak (M+H)$^+$: 563. Found: molecular peak (M+H)$^+$: 563.

EXAMPLE 95

9-[4-(4-quinolin-2-yl-piperazin-1-yl)-butyl]-9H-fluorene-9-carboxylic acid-(methoxycarbonyl-methyl)-amide a. 9-(4-bromo-butyl)-9H-fluorene-9-carboxylic acid-(methoxycarbonyl-methyl)-amide Prepared analogously to Example 1 from glycine-methyl ester and 9-(4-bromo-butyl)-9H-fluorene-9-carboxylic acid chloride.

Yield: 1.36 g (47.5% of theory), Melting point: 84° C. $C_{21}H_{22}BrNO_3$ (M=416.31) Calc.: molecular peak (M+H)$^+$: 416/418. Found: molecular peak (M+H)$^+$: 416/418.

b. 9-[4-(4-quinolin-2-yl-piperazin-1-yl)-butyl]-9H-fluorene-9-carboxylic acid-(methoxycarbonyl-methyl)-amide Prepared analogously to Example 2 from 9-(4-bromo-butyl)-9H-fluorene-9-carboxylic acid-(methoxycarbonyl-methyl)-amide and 2-piperazin-1-yl-quinoline.

Yield: 0.1 g (25.5% of theory), Melting point: 53–55° C. $C_{34}H_{36}N_4O_3$ (M=548.69) Calc.: molecular peak (M+H)$^+$: 549. Found: molecular peak (M+H)$^+$: 549.

EXAMPLE 96

9-[4-(4-quinolin-2-yl-piperazin-1-yl)-butyl]-9H-fluorene-9-carboxylic acid-(2-carboxy-ethyl)-amide A solution of 0.08 g (0.142 mmol) of 9-[4-(4-quinolin-2-yl-piperazin-1-yl)-butyl]-9H-fluorene-9-carboxylic acid-(2-methoxycarbonyl-ethyl)-amide in 2 ml of 2N sodium hydroxide solution and 35 ml of methanol is stirred for 14 hours at ambient temperature. Then the mixture is concentrated by evaporation, diluted with water and adjusted to a pH of 5 with 1N hydrochloric acid. The precipitate formed is filtered off.

Yield: 0.05 g (64.2% of theory), Melting point: 98–100° C. $C_{34}H_{36}N_4O_3$ (M=548.69) Calc.: molecular peak (M+H)$^+$: 549. Found: molecular peak (M+H)$^+$: 549.

EXAMPLE 97

9-[4-(4-quinolin-2-yl-piperazin-1-yl)-butyl]-9H-fluorene-9-carboxylic acid-(carboxy-methyl)-amide Prepared analogously to Example 96 from 9-[4-(4-quinolin-2-yl-piperazin-1-yl)-butyl]-9H-fluorene-9-carboxylic acid-(carboxy-methyl)-amide and sodium hydroxide solution.

Yield: 0.04 g (34.2% of theory), Melting point: 127–129° C. $C_{33}H_{34}N_4O_3$ (M=534.66) Calc.: molecular peak (M+H)$^+$: 535. Found: molecular peak (M+H)$^+$: 535.

EXAMPLE 98

9-[4-(cis-2,6-dimethyl-4-quinolin-2-yl-piperazin-1-yl)-butyl]-9H-fluorene-9-carboxylic acid-3,4-difluoro-benzylamide 9-[4-(cis-2,6-dimethyl-4-quinolin-2-yl-piperazin-1-yl)-butyl]-9H-fluorene-9-carboxylic acid-3,4-difluoro-benzylamide Prepared analogously to Example 2 from 9-(4-bromo-butyl)-9H-fluorene-9-carboxylic acid-3,4-difluoro-benzylamide and 2-(cis-3,5-dimethyl-piperazin-1-yl)-quinoline.

Yield: 0.09 g (22.4% of theory), Melting point: 162° C. $C_{40}H_{40}F_2N_4O$ (M=630.78) Calc.: molecular peak (M+H)$^+$: 631. Found: molecular peak (M+H)$^+$: 631.

EXAMPLE 99

9-[4-(4-benzothiazol-2-yl-[1.4]diazepan-1-yl)-butyl]-9H-fluorene-9-carboxylic acid-Propylamide Prepared analogously to Example 1 from 9-(4-bromo-butyl)-9H-fluorene-9-carboxylic acid-propylamide and 2-[1.4]diazepan-1-yl-benzothiazole.

Yield: 0.14 g (30.3% of theory), $C_{33}H_3BN_4OS$ (M=538.76) Calc.: molecular peak (M+H)$^+$: 539. Found: molecular peak (M+H)$^+$: 539.

EXAMPLE 100

9-[4-(4-benzothiazol-2-yl-piperazin-1-yl)-butyl]-9H-xanthene-9-carboxylic acid-(2,2,2-trifluoro-ethyl)-amide a. 9-(4-bromo-butyl)-9H-xanthene-9-carboxylic acid Prepared analogously to Example 1a from 9-xanthenecarboxylic acid and dibromobutane.

Yield: 24 g (70.2% of theory), $C_{18}HL_7BrO_3$ (M=361.23) Calc.: molecular peak (M–H)$^-$: 359/61. Found: molecular peak (M–H)$^-$: 359/61.

b. 9-(4-bromo-butyl)-9H-xanthene-9-carboxylic acid chloride

Prepared analogously to Example 1b from 9-(4-bromo-butyl)-9H-xanthene-9-carboxylic acid and oxalyl chloride.

Yield: 10.6 g (97% of theory) c. 9-(4-bromo-butyl)-9H-xanthene-9-carboxylic acid-(2,2,2-trifluoro-ethyl)-amide Prepared analogously to Example 1c from 2,2,2-trifluoroethylamine-hydrochloride and 9-(4-bromo-butyl)-9H-xanthene-9-carboxylic acid chloride.

Yield: 10 g (80.5% of theory), $C_{20}H_{19}BrF_3NO_2$ (M=442.27) Calc.: molecular peak (M−H)⁻: 440/2. Found: molecular peak (M−H)⁻: 440/2.

d. 9-[4-(4-benzothiazol-2-yl-piperazin-1-yl)-butyl]-9H-xanthene-9-carboxylic acid-(2,2,2-trifluoro-ethyl)-amide Prepared analogously to Example 1f from 9-(4-bromo-butyl)-9H-xanthene-9-carboxylic acid-(2,2,2-trifluoro-ethyl)-amide and 2-(piperazin-1-yl)-benzothiazole.

Yield: 0.18 g (45.7% of theory), Melting point: 58–62° C. $C_{31}H_{31}F_3N_4O_2S$ (M=580.67) Calc.: molecular peak (M+H)⁺: 581. Found: molecular peak (M+H)⁺: 581.

EXAMPLE 101

9-[4-(4-benzoxazol-2-yl-piperazin-1-yl)-butyl]-9H-xanthene-9-carboxylic acid-(2,2,2-trifluoro-ethyl)-amide Prepared analogously to Example 2b from 9-(4-bromo-butyl)-9H-xanthene-9-carboxylic acid-(2,2,2-trifluoro-ethyl)-amide and 2-(piperazin-1-yl)-benzoxazole.

Yield: 0.22 g (43.1% of theory), Melting point: 196–197° C. $C_{31}H_{31}F_3N_4O_3$ (M=564.61) Calc.: molecular peak (M+H)⁺: 565. Found: molecular peak (M+H)⁺: 565.

EXAMPLE 102

9-{4-[4-(1-methyl-1H-benzimidazol-2-yl)-piperazin-1-yl]-butyl}-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 1-methyl-2-piperazin-1-yl-1H-benzimidazole.

Yield: 0.1 g (25.4% of theory), Melting point: 110° C. $C_{32}H_{34}F_3N_5O_2$ (M=577.65) Calc.: molecular peak (M+H)⁺: 578. Found: molecular peak (M+H)⁺: 578.

EXAMPLE 103

9-[4-(4-quinolin-2-yl-piperazin-1-yl)-butyl]-9H-xanthene-9-carboxylic acid-(2,2,2-trifluoro-ethyl)-amide Prepared analogously to Example 2b from 9-(4-bromo-butyl)-9H-xanthene-9-carboxylic acid-(2,2,2-trifluoro-ethyl)-amide and 2-(piperazin-1-yl)-quinoline.

Yield: 0.12 g (30.8% of theory), Melting point: 178° C. $C_{33}H_{33}F_3N_4O_2$ (M=574.65) Calc.: molecular peak (M+H)⁺: 575. Found: molecular peak (M+H)⁺: 575.

EXAMPLE 104

9-{4-[4-(5-chloro-quinolin-2-yl)-piperazin-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 5-chloro-2-piperazin-1-yl-quinoline.

Yield: 0.22 g (79.9% of theory), Melting point: 160° C. $C_{33}H_{32}ClF_3N_4O_2$ (M=609.09) Calc.: molecular peak (M+H)⁺: 609/611. Found: molecular peak (M+H)⁺: 609/611.

EXAMPLE 105

9-{4-[4-(6-chloro-quinolin-2-yl)-piperazin-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 6-chloro-2-piperazin-1-yl-quinoline.

Yield: 0.23 g (34.5% of theory), Melting point: 165° C. $C_{33}H_{32}ClF_3N_4O_2$ (M=609.09) Calc.: molecular peak (M+H)⁺: 609/611. Found: molecular peak (M+H)⁺: 609/611.

EXAMPLE 106

9-{4-[4-(8-chloro-quinolin-2-yl)-piperazin-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 8-chloro-2-piperazin-1-yl-quinoline. Melting point: 68° C. $C_{33}H_{32}ClF_3N_4O_2$ (M=609.09) Calc.: molecular peak (M+H)⁺: 609/611. Found: molecular peak (M+H)⁺: 609/611.

EXAMPLE 107

9-{4-[4-(8-methoxy-quinolin-2-yl)-piperazin-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 8-methoxy-2-piperazin-1-yl-quinoline.

Yield: 0.1 g (29.3% of theory), Melting point: 75° C. $C_{34}H_{35}F_3N_4O_3$ (M=604.67) Calc.: molecular peak (M+H)⁺: 605. Found: molecular peak (M+H)⁺: 605.

EXAMPLE 108

9-[4-(4-quinoxalin-2-yl-piperazin-1-yl)-butyl]-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 2-(piperazin-1-yl)-quinoxaline.

Yield: 0.19 g (48.7% of theory), Melting point: from 140° C. decomposition $C_{32}H_{32}F_3N_5O_2$ (M=575.63) Calc.: molecular peak (M−H)⁻: 574. Found: molecular peak (M−H)⁻: 574.

EXAMPLE 109

9-{4-[(S)-2-methyl-4-quinolin-2-yl-piperazin-1-yl]-butyl}-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 2-[(S)-3-methyl-piperazin-1-yl]-quinoline Yield: 0.034 g (7.3% of theory), Melting point: 52–53° C. $C_{34}H_{35}F_3N_4O_2$ (M=588.67) Calc.: molecular peak (M+H)⁺: 589. Found: molecular peak (M+H)⁺: 589.

EXAMPLE 110

9-[4-(4-benzothiazol-2-yl-cis-2,6-dimethyl-piperazin-1-yl)-butyl]-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 2-(cis-3,5-dimethyl-piperazin-1-yl)-benzothiazole.

Yield: 0.09 g (21.8% of theory), Melting point: 157° C. $C_{33}H_{35}F_3N_4O_2S$ (M=608.73) Calc.: molecular peak (M−H)⁻: 607. Found: molecular peak (M−H)⁻: 607.

EXAMPLE 111

9-[4-(cis-2,6-dimethyl-4-quinolin-2-yl-piperazin-1-yl)-butyl]-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 2-(cis-3,5-dimethyl-piperazin-1-yl)-quinoline Yield: 0.09 g (16.5% of theory), Melting point: 177° C. $C_{35}H_{37}F_3N_4O_2$ (M=602.70) Calc.: molecular peak $(M+H)^+$: 603. Found: molecular peak $(M+H)^+$: 603.

EXAMPLE 112

9-{4-[4-(5-chloro-quinolin-2-yl)-cis-2,6-dimethyl-piperazin-1-yl]-butyl}-9H-xanthene-9-carboxylic acid(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 5-chloro-2-(cis-3,5-dimethyl-piperazin-1-yl)-quinoline.

Yield: 0.2 g (46.3% of theory), Melting point: 182° C. $C_{35}H_{36}ClF_3N_4O_2$ (M=637.15) Calc.: molecular peak $(M+H)^+$: 637/639. Found: molecular peak $(M+H)^+$: 637/639.

EXAMPLE 113

9-[4-(4-benzothiazol-2-yl-[1.4]diazepan-1-yl)-butyl]-9H-xanthene-9-carboxylic acid-(2,2,2-trifluoro-ethyl)-amide Prepared analogously to Example 1 from 9-(4-bromo-butyl)-9H-xanthene-9-carboxylic acid-(2,2,2-trifluoro-ethyl)-amide and 2-[1.4]diazepan-1-yl-benzothiazole.

Yield: 0.45 g (58.8% of theory), Melting point: 85° C. foam $C_{32}H_{33}F_3N_4O_2S$ (M=594.70) Calc.: molecular peak $(M+H)^+$: 595. Found: molecular peak $(M+H)^+$: 595.

EXAMPLE 114

9-{4-[4-(1-methyl-1H-benzimidazol-2-yl)-[1.4]diazepan-1-yl]-butyl}-9H-fluorene-9-carboxylic acid-(2,2,2-trifluoro-ethyl)-amide Prepared analogously to Example 2 from 9-(4-bromo-butyl)-9H-fluorene-9-carboxylic acid-(2,2,2-trifluoro-ethyl)-amide and 2-[1.4]diazepan-1-yl-1-methyl-1H-benzimidazole.

Yield: 0.23 g (42.6% of theory), Melting point: 72° C. $C_{33}H_{36}F_3N_5O$ (M=575.68) Calc.: molecular peak $(M+H)^+$: 576. Found: molecular peak $(M+H)^+$: 576.

EXAMPLE 115

9-{4-[4-(1-methyl-1H-benzimidazol-2-yl)-[1.4]diazepan-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 2-[1.4]diazepan-1-yl-1-methyl-1H-benzimidazole.

Yield: 0.2 g (49.9% of theory), Melting point: 79° C. $C_{33}H_{36}F_3N_5O_2$ (M=591.68) Calc.: molecular peak $(M+H)^+$: 592. Found: molecular peak $(M+H)^+$: 592.

EXAMPLE 116

9-[4-(4-quinolin-2-yl-[1.4]diazepan-1-yl)-butyl]-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 2-[1.4]diazepan-1-yl-quinoline.

Yield: 0.27 g (50.7% of theory), $C_{34}H_{35}F_3N_4O_2$ (M=588.67) Calc.: molecular peak $(M+H)^+$: 589. Found: molecular peak $(M+H)^+$: 589.

EXAMPLE 117

9-{4-[4-(6-chloro-quinolin-2-yl)-[1.4]diazepan-1-yl]-butyl}-9H-xanthene-9-carboxylic acid-(2,2,2-trifluoro-ethyl)-amide Prepared analogously to Example 2 from 9-(4-bromo-butyl)-9H-xanthene-9-carboxylic acid-(2,2,2-trifluoro-ethyl)-amide and 6-chloro-2-[1.4]diazepan-1-yl-quinoline Yield: 0.22 g (39.1% of theory), Melting point: 69° C. $C_{34}H_{34}ClF_3N_4O_2$ (M=623.12) Calc.: molecular peak $(M+H)^+$: 623/625. Found: molecular peak $(M+H)^+$: 623/625.

EXAMPLE 118

9-[4-(4-quinolin-2-yl-piperazin-1-yl)-butyl]-9H-xanthene-9-carboxylic acid-Butylamide a. 9-(4-bromo-butyl)-9H-xanthene-9-carboxylic acid-Butylamide Prepared analogously to Example 1 from n-butylamine and 9-(4-bromo-butyl)-9H-xanthene-9-carboxylic acid chloride.

Yield: 0.3 g (45.6% of theory), $C_{22}H_{26}BrNO_2$ (M=416.36) Calc.: molecular peak $(M+H)^+$: 416/418. Found: molecular peak $(M+H)^+$: 416/418.

b. 9-[4-(4-quinolin-2-yl-piperazin-1-yl)-butyl]-9H-xanthene-9-carboxylic acid-Butylamide Prepared analogously to Example 1 from 9-(4-bromo-butyl)-9H-xanthene-9-carboxylic acid-butylamide and 2-piperazin-1-yl-quinoline.

Yield: 0.12 g (45.6% of theory), Melting point: 45–53° C. $C_{35}H_{40}N_4O_2$ (M=548.73) Calc.: molecular peak $(M+H)^+$: 549. Found: molecular peak $(M+H)^+$: 549.

EXAMPLE 119

9-[4-(4-quinolin-2-yl-piperazin-1-yl)-butyl]-9H-xanthene-9-carboxylic acid-4-fluoro-benzylamide a. 9-(4-bromo-butyl)-9H-xanthene-9-carboxylic acid-4-fluoro-benzylamide Prepared analogously to Example 1 from 4-fluoro-benzylamine and 9-(4-bromo-butyl)-9H-xanthene-9-carboxylic acid chloride.

Yield: 1.25 g (63.3% of theory), $C_{25}H_{23}BrFNO_2$ (M=468.37) Calc.: molecular peak $(M+H)^+$: 468/470. Found: molecular peak $(M+H)^+$: 468/470.

b. 9-[4-(4-quinolin-2-yl-piperazin-1-yl)-butyl]-9H-xanthene-9-carboxylic acid-4-fluoro-benzylamide Prepared analogously to Example 1 from 9-(4-bromo-butyl)-9H-xanthene-9-carboxylic acid-4-fluoro-benzylamide and 2-piperazin-1-yl-quinoline.

Yield: 0.04 g (10.4% of theory), $C_{38}H_{37}FN_4O_2$ (M=600.74) Calc.: molecular peak $(M+H)^+$: 601. Found: molecular peak $(M+H)^+$: 601.

EXAMPLE 120

1-morpholin-4-yl-1-{9-[4-(4-quinolin-2-yl-piperazin-1-yl)-butyl]-9H-xanthene-9-yl}-methanone a. 1-[9-(4-bromo-butyl)-9H-xanthene-9-yl]-1-morpholin-4-yl-methanone Prepared analogously to Example 1 from morpholine and 9-(4-bromo-butyl)-9H-xanthene-9-carboxylic acid chloride.

Yield: 0.2 g (29.4% of theory), $C_{22}H_{24}BrNO_3$ (M=430.34) Calc.: molecular peak (M+H)$^+$: 430/432. Found: molecular peak (M+H)$^+$: 430/432.

b. 1-morpholin-4-yl-1-{9-[4-(4-quinolin-2-yl-piperazin-1-yl)-butyl]-9H-xanthene-9-yl}-methanone Prepared analogously to Example 1 from 1-[9-(4-bromo-butyl)-9H-xanthen-9-yl]-1-morpholin-4-yl-methanone and 2-piperazin-1-yl-quinoline.

Yield: 0.15 g (57.3% of theory), Melting point: 48–58° C. $C_{35}H_{38}N_4O_3$ (M=562.71) Calc.: molecular peak (M+H)$^+$: 563. Found: molecular peak (M+H)$^+$: 563.

EXAMPLE 121

9-[4-(4-(quinolin-2-yl)-piperazin-1-yl)-propyl]-9H-fluorene-9-carboxylic acid-(2,2,2-trifluoro-ethyl)-amide a. 9-allyl-9H-fluorene-9-carboxylic acid 42 ml (0.096 mol) of a 2.5M butyl lithium solution are added dropwise at 0° C. under nitrogen to a solution of 10 g (0.048 mol) of 9-fluorenecarboxylic acid in 150 ml of THF and the mixture is stirred for 30 minutes. Then 4.67 ml (0.054 mol) of allyl bromide are added and the solution is stirred for four hours at ambient temperature. The reaction solution is poured into water and extracted with diethyl ether. The aqueous phase is acidified with 1N hydrochloric acid and extracted with dichloromethane. The organic phase is dried over sodium sulphate and freed from solvent.

Yield: 2.4 g (20% of theory), $C_{17}H_{14}O_2$ (M=250.30) Calc.: molecular peak (M+Na)$^+$: 273. Found: molecular peak (M+Na)$^+$: 273.

b. 9-allyl-9H-fluorene-9-carboxylic acid chloride

Prepared analogously to Example 1 from 9-allyl-9.H-fluorene-9-carboxylic acid and oxalyl chloride.

Yield: 2 g (93.1% of theory), c. 9-allyl-9H-fluorene-9-carboxylic acid-(2,2,2-trifluoro-ethyl)-amide Prepared analogously to Example 1 from 9-allyl-9H-fluorene-9-carboxylic acid chloride and 2,2,2-trifluoroethylamine-hydrochloride.

Yield: 1.65 g (66.9% of theory), Melting point: 81° C. $C_{19}H_{16}F_3NO$ (M=331.34) Calc.: molecular peak (M+H)$^+$: 332. Found: molecular peak (M+H)$^+$: 332.

d. 9-(3-hydroxy-propyl)-9H-fluorene-9-carboxylic acid-(2,2,2-trifluoro-ethyl)-amide 12 ml of 9-borabicyclo[3.3.1]nonane are added dropwise to a solution of 1.5 g (4.52 mmol) of 9-allyl-9H-fluorene-9-carboxylic acid-(2,2,2-trifluoro-ethyl)-amide in 40 ml of THF under nitrogen. Then the mixture is stirred for three hours at ambient temperature. 6 ml of 1M sodium hydroxide solution and 4 ml of 33% hydrogen peroxide solution are then added successively and the resulting mixture is stirred for one hour. The reaction mixture is poured into water and extracted with ethyl acetate. The organic phase is dried over sodium sulphate. The product is purified by column chromatography on silica gel (eluant: cyclohexane/ethyl acetate=1:1).

Yield: 1.07 g (67.7% of theory), Melting point: 109° C. $C_{19}H_{18}F_3NO_2$ (M=349.35) Calc.: molecular peak (M+H)$^+$: 350. Found: molecular peak (M+H)$^+$: 350.

e. 9-(4-bromo-propyl)-9H-fluorene-9-carboxylic acid-(2,2,2-trifluoro-ethyl)-amide 2.132 g (6.43 mmol) of tetrabromomethane are added to a solution of 1.07 g (3.06 mmol) of 9-(3-hydroxy-propyl)-9H-fluorene-9-carboxylic acid-(2,2,2-trifluoro-ethyl)-amide in 50 ml of dichloromethane. Then 1.687 g (6.43 mmol) of triphenyl-phosphine are added and the reaction mixture is stirred for 14 hours at ambient temperature. The solvent is then distilled off. The product is purified by column chromatography on silica gel (eluant: cyclohexane/ethyl acetate=3:1).

Yield: 0.88 g (69.7% of theory), Melting point: 99° C. $C_{19}H_{17}BrF_3NO$ (M=412.25) Calc.: molecular peak (M+H)$^+$: 412/414. Found: molecular peak (M+H)$^+$: 412/414.

f. 9-[4-(4-(quinolin-2-yl)-piperazin-1-yl)-propyl]-9H-fluorene-9-carboxylic acid-(2,2,2-trifluoro-ethyl)-amide Prepared analogously to Example 2 from 9-(4-bromo-propyl)-9H-fluorene-9-carboxylic acid-(2,2,2-trifluoro-ethyl)-amide and 2-(piperazin-1-yl-quinoline.

Yield: 0.08 g (24.2% of theory), Melting point: 58° C. $C_{32}H_{31}F_3N_4O$ (M=544.62) Calc.: molecular peak (M+H)$^+$: 545. Found: molecular peak (M+H)$^+$: 545.

EXAMPLE 122

9-[3-(4-benzothiazol-2-yl-piperazin-1-yl)-propyl]-9H-fluorene-9-carboxylic acid-(2,2,2-trifluoro-ethyl)-amide Prepared analogously to Example 2 from 9-(4-bromo-propyl)-9H-fluorene-9-carboxylic acid-(2,2,2-trifluoro-ethyl)-amide and 2-piperazin-1-yl-benzothiazole.

Yield: 0.12 g (36% of theory), Melting point: 68° C. $C_{32}H_{31}F_3N_4O$ (M=544.62) Calc.: molecular peak (M+H)$^+$: 551. Found: molecular peak (M+H)$^+$: 551.

EXAMPLE 123

9-[4-(4-quinolin-2-yl-[1.4]diazepan-1-yl)-propyl]-9H-fluorene-9-carboxylic acid-(2,2,2-trifluoro-ethyl)-amide Prepared analogously to Example 2 from 9-(4-bromo-propyl)-9H-fluorene-9-carboxylic acid-(2,2,2-trifluoro-ethyl)-amide and 2-[1.4]diaepan-1-yl-quinoline.

Yield: 0.09 g (29.3% of theory), Melting point: 72° C. $C_{33}H_{33}F_3N_4O$ (M=558.65) Calc.: molecular peak (M+H)$^+$: 559. Found: molecular peak (M+H)$^+$: 559.

The following compounds may be prepared analogously to Examples 100–120:

(1) 9-{4-[4-(6-fluoro-quinolin-2-yl)-piperazin-1-yl]-butyl}-9H-xanthene-9-carboxylic acid-(2,2,2-trifluoro-ethyl)-amide (2) 9-{4-[4-(6-bromo-quinolin-2-yl)-piperazin-1-yl]-butyl}-9H-xanthene-9-carboxylic acid-(2,2,2-trifluoro-ethyl)-amide (3) 9-{4-[4-(6-trifluoromethyl-quinolin-2-yl)-piperazin-1-yl]-butyl}-9H-xanthene-9-carboxylic acid-(2,2,2-trifluoro-ethyl)-amide (4) 9-{4-[4-(6-methyl-quinolin-2-yl)-piperazin-1-yl]-butyl}-9H-xanthene-9-carboxylic acid-(2,2,2-trifluoro-ethyl)-amide (5) 9-{4-[4-(6-methoxy-quinolin-2-yl)-piperazin-1-yl]-butyl}-9H-xanthene-9-carboxylic acid-(2,2,2-trifluoro-ethyl)-amide (6) 9-[4-(4-quinazolin-2-yl-piperazin-1-yl)-butyl]-9H-xanthene-9-carboxylic acid-(2,2,2-trifluoro-ethyl)-amide

EXAMPLE 124

Tablets Containing 5 mg of Active Substance Per Tablet
Composition:

| | |
|---|---|
| active substance | 5.0 mg |
| lactose monohydrate | 70.8 mg |
| microcrystalline cellulose | 40.0 mg |
| sodium carboxymethylcellulose, insolubly crosslinked | 3.0 mg |
| magnesium stearate | 1.2 mg |

Preparation:

The active substance is mixed for 15 minutes with lactose monohydrate, microcrystalline cellulose and sodium carboxymethylcellulose in a suitable diffusion mixer. Magnesium stearate is added and mixed with the other substances for another 3 minutes.

The finished mixture is compressed in a tablet press to form facetted flat round tablets.

Diameter of the tablet: 7 mm
Weight of the tablet: 120 mg

EXAMPLE 125

Capsules Containing 50 mg of Active Substance Per Capsule
Composition:

| | |
|---|---|
| active substance | 50.0 mg |
| lactose monohydrate | 130.0 mg |
| corn starch | 65.0 mg |
| highly dispersed silicon dioxide | 2.5 mg |
| magnesium stearate | 2.5 mg |

Preparation:

A starch paste is prepared by swelling some of the corn starch in a suitable amount of hot water. The paste is then left to cool to room temperature.

The active substance is premixed for 15 minutes in a suitable mixer with lactose monohydrate and corn starch. The starch paste is added and the mixture is mixed with sufficient water to produce a moist !homogeneous mass. The moist mass is passed through a screen with a mesh size of 1.6 mm. The screened granules are dried on racks at about 55° C. for 12 hours.

The dried granules are then passed through screens with mesh sizes of 1.2 and 0.8 mm. Highly dispersed silica is mixed with the granules in a suitable mixer for 3 minutes. Then magnesium stearate is added and mixing is continued for another 3 minutes.

The finished mixture is packed into empty size 1 hard gelatine capsule shells using a capsule filling machine.

EXAMPLE 126

Tablets Containing 200 mg of Active Substance Per Tablet
Composition:

| | |
|---|---|
| active substance | 200.0 mg |
| lactose-monohydrate | 167.0 mg |
| microcrystalline cellulose | 80.0 mg |
| hydroxypropyl-methylcellulose, type 2910 | 10.0 mg |
| poly-1-vinyl-2-pyrrolidone, insolubly crosslinked | 20.0 mg |
| magnesium stearate | 3.0 mg |

Preparation:

HPMC is dispersed in hot water. After cooling, the mixture yields a clear solution.

The active substance is premixed in a suitable mixer for 5 minutes with lactose monohydrate and microcrystalline cellulose. The HPMC solution is added and the mixing is continued until a homogeneous moist composition is obtained. The moist composition is passed through a screen with a mesh size of 1.6 mm. The screened granules are dried on racks at about 55° C. for 12 hours.

The dried granules are then passed through screens with mesh sizes of 1.2 and 0.8 mm. Poly-1-vinyl-2-pyrrolidone is mixed with the granules in a suitable mixer for 3 minutes. Then magnesium stearate is added and mixing is continued for another 3 minutes.

The finished mixture is compressed in a tablet press to form oblong tablets (16.2×7.9 mm).

Weight of a tablet: 480 mg

What is claimed is:

1. Substituted piperazine derivatives having general formula

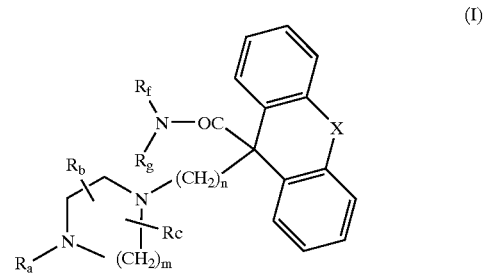

(I)

wherein m denotes the number 2 or 3, n denotes the number 1, 2, 3, 4 or 5,

X denotes a carbon-carbon bond, or an oxygen atom $R_a$ denotes $R_a$ denotes a naphthyl, quinolinyl, quinazolinyl, quinoxalinyl, benzoxazolyl, benzothiazolyl, or benzimidazolyl, group, each of which is connected to the nitrogen atom of the adjacent piperazino group via a carbon atom in the bicyclic group, wherein the phenyl moiety of the said bicyclic groups may be monosubstituted by a trifluoromethyl or nitro group or mono- or disubstituted by fluorine, chlorine or bromine atoms or by methyl, methoxy or ethoxy groups, wherein the substituents may be identical or different, and any imino group present in said bicyclic groups may additionally be substituted by a $C_{1-3}$-alkyl, phenyl-$C_{1-3}$-alkyl, phenyl or pyridyl group $R_b$ and $R_c$ independently of one another in each case denote a hydrogen atom or a $C_{1-3}$-alkyl group, $R_f$ and $R_g$, which may be identical or different, denote hydrogen atoms or $C_{1-6}$-alkyl groups wherein the hydrogen atoms of the alkyl may be wholly or partly replaced by fluorine atoms, $C_{3-7}$-cycloalkyl, phenyl, $C_{1-3}$-alkoxy-carbonyl-$C_{1-2}$-alkyl, carboxy-$C_{1-2}$-alkyl, methoxy-$C_{2-3}$-alkyl, or phenyl-$C_{1-3}$-alkyl groups, wherein said phenyl groups may be mono-, di- or tri-substituted in the carbon skeleton by fluorine, chlorine or bromine atoms, by $C_{1-3}$-alkyl or $C_{1-3}$-alkoxy groups wherein the hydrogen atoms of the alkyl may be wholly or partially replaced by fluorine atoms, by hydroxy, carboxy, $C_{1-3}$-alkoxycarbonyl, aminocarbonyl, $C_{1-3}$-alkylaminocarbonyl, N,N-di-($C_{1-3}$-alkyl)-aminocarbonyl, N,N-di-($C_{1-3}$-alkyl)-amino, nitro or amino groups, wherein the substituents may be identical or different, wherein the tricyclic group in said general formula I may be mono- or disubstituted by fluorine or chlorine atoms, by methyl or methoxy groups and the substituents may be identical or different, the enantiomers, diastereomers and salts thereof.

2. Substituted piperazine derivatives of general formula I according to claim 1, wherein n denotes the number 3, 4 or 5 and m, X, $R_a$, $R_b$, $R_c$, $R_f$ and $R_g$ are defined as in claim 1, the isomers and salts thereof.

3. Substituted piperazine derivatives of general formula I according to claim 1, wherein n denotes the number 3, 4 or 5, X denotes a carbon-carbon bend or an oxygen atom, $R_g$ denotes a hydrogen atom, the isomers and salts thereof.

4. Substituted piperazine derivatives of general fonnula I according to claim 1, wherein m denotes the number 2, n denotes the number 4, X denotes a carbon-carbon bond or an oxygen atom, $R_a$ denotes a naphthyl, quinolinyl, quinazolinyl, benzoxazolyl, benzothiazolyl, or benzimidazolyl group each of which is connected to the nitrogen atom of the adjacent piperazino group via a carbon atom in the bicyclic group, wherein any imino group present in said bicyclic groups may additionally be substituted by a $C_{1-3}$-alkyl, phenyl-$C_{1-3}$-alkyl, phenyl or pyridyl group, $R_b$ and $R_c$ independently of one another each denote a hydrogen atom or a methyl group, $R_f$ denotes a hydrogen atom, a $C_{1-6}$-alkyl group wherein the hydrogen atoms of the alkyl may be wholly or partly replaced by fluorine atoms, a $C_{3-7}$-cycloalkyl, $C_{1-3}$-alkoxy-carbonyl-$C_{1-2}$-alkyl, carboxy-$C_{1-2}$-alkyl, methoxy-$C_{2-3}$-alkyl, phenyl, or phenyl-$C_{1-3}$-alkyl group, wherein said phenyl groups may be substituted in each case by one or two fluorine, chlorine or bromine atoms or by one or two $C_{1-3}$-alkyl or $C_{1-3}$-alkoxy groups wherein the hydrogen atoms of the alkyl may be wholly or partially replaced by fluorine atoms, and $R_g$ denotes a hydrogen atom, the isomers and salts thereof.

5. Physiologically acceptable salts of the compounds according to claims 1.

6. Medicaments, comprising a compound according to claim 1 together with one or more inert carriers and/or diluents.

7. A method of treating a disease selected from the list consisting of hyperlipidaemias, atherosclerosis diabetes mellitus, adiposity and pancreatitis comprising treating a patient in need thereof with a therapeutic amount of a compound of claim 1.

* * * * *